US007354728B2

(12) United States Patent
Dechering et al.

(10) Patent No.: US 7,354,728 B2
(45) Date of Patent: Apr. 8, 2008

(54) COACTIVATION OF NUCLEAR RECEPTORS

(75) Inventors: Koen Jacob Dechering, Nijmegen (NL); Sietse Mosselman, Oss (NL)

(73) Assignee: N.V. Organon, Oss (NL)

( * ) Notice: Subject to any disclaimer, the term of this patent is extended or adjusted under 35 U.S.C. 154(b) by 343 days.

(21) Appl. No.: 10/362,463

(22) PCT Filed: Aug. 16, 2001

(86) PCT No.: PCT/EP01/09499

§ 371 (c)(1),
(2), (4) Date: Aug. 27, 2003

(87) PCT Pub. No.: WO02/16426

PCT Pub. Date: Feb. 28, 2002

(65) Prior Publication Data

US 2004/0059089 A1    Mar. 25, 2004

(30) Foreign Application Priority Data

Aug. 21, 2000 (EP) .................................. 00202905
May 14, 2001 (EP) .................................. 01201771

(51) Int. Cl.
*G01N 33/53* (2006.01)
*C12N 5/00* (2006.01)
*C07K 1/00* (2006.01)

(52) U.S. Cl. ........................ 435/7.8; 435/7.1; 435/325; 530/350

(58) Field of Classification Search ..................... None
See application file for complete search history.

(56) References Cited

FOREIGN PATENT DOCUMENTS

| EP | 1 074 617 A | 2/2001 |
| WO | 97 10337 A | 3/1997 |
| WO | 98 30582 A | 7/1998 |
| WO | 99 64596 A | 12/1999 |
| WO | 01 75067 | 10/2001 |

OTHER PUBLICATIONS

Nagase et al. 1998. DNA Research 5:31-39.*
McKenna et al. 1999. Endocrine Reviews. 20:321-344.*
Watanabe et al. 1997. BBRC 236:140-145.*
Nagase, T. et al.: "Prediction of the Coding Sequences of Unidentified Human Genes. IX. The Complete Sequences of 100 New cDNA Clones from Brain Which Can Code for Large Proteins in vitro"; DNA Research, vol. 5, No. 1, Feb. 28, 1998, pp. 31-39.
Meijer, O.C. et al: "Differential Expression and Regional Distribution of Steroid Receptor Coactivators SRC-1 and SRC-2 in Brain and Pituitary"; ENDOCRINOLOGY, vo. 141, No. 6, Jun. 2000, pp. 2192-2199.
Dechering, K. et al: "Estrogen Receptors alpha and beta: Two Receptors of a Kind?"; Current Medicinal Chemistry, vol. 7, No. 5, May 2000, pp. 561-576.
Glass, C.K. et al: "Nuclear receptor coactivators"; Current Opinion in Cell Biology, vol. 9, No. 2, Apr. 1997, pp. 222-232.
Henikoff et al., "Amino acid substitution matrices from protein blocks," Proc Natl Acad Sci USA 89 (1992) 10915-10919.
Hong et al., "GRIP1, a Transcriptional Coactivator for the AF-2 Transactivation Domain of Steroid, Thyroid, Retinoid, and Vitamin D. Receptors," Mol Cell Biol 17 (1997) 2735-2744.
Lyttle et al., "Human Estrogen Receptor Regulation in a Yeast Model System and Studies on Receptor Agonists and Antagonists," Steroid Biochem Biol 42 (1992) 677-685.
Needleman et al., "A General Method Applicable to the Search for Similarities in the Amino Acid Sequence of Two Proteins," J Mol Biol 48 (1970) 443-453.
Nishikawa et al., "New Screening Methods for Chemicals with Hormonal Activities Using Interaction of Nuclear Hormone Receptor with Coactivator," Toxicol Appl Pharmacol 154 (1999) 76-83.
Oñate et al., "Sequence and Characterization of a Coactivator for the Steroid Hormone Receptor Superfamily," Science 270 (1995) 1354-1357.
Paech et al., "Differential Ligand Activation of Estrogen Receptors ERα and ERβ at AP1 Sites," Science 277 (1997) 1508-1510.
Stam et al., "Genomic Organization, Coding Sequence and Functional Expression of Human $5\text{-}HT_2$ and $5\text{-}HT_{1A}$ Receptor Genes," Eur J. Pharmacol 227 (1992) 153-162.
Zou et al., "Estrogen Receptor β Activates the Human Retinoic Acid Receptor α-1 Promoter in Response to Tamoxifen and Other Estrogen Receptor Antagonists, but Not in Response to Estrogen," Mol Endocrinol 13 (1999) 418-430.

* cited by examiner

*Primary Examiner*—Manjunath N. Rao
*Assistant Examiner*—Shulamith H Shafer
(74) *Attorney, Agent, or Firm*—Susan Hess

(57) ABSTRACT

The invention provides a protein having an amino acid sequence as in SEQ ID 7, 8, 11 or 12, similar proteins, naturally occurring variants and homologous functional equivalents thereof, as well as the use of a polynucleotide encoding such protein, for use in an assay and for use in a method of modulation of transcriptional activity promoted by a responsive nuclear receptor and a coactivator, which coactivator is the mentioned protein and is named COASTER, and which nuclear receptor is preferably a steroid receptor.

19 Claims, 13 Drawing Sheets

Figure 1

```
            ->RACE fragment 1
            GGAAGCCCGGGAGTGAGAGAAAGCGGCTCCGGGGGCATAGCGGGCCAGTAAGGGCCGCTC
            CTCCTTTGAAGAGGTTTTGCGTCTCTTTCCGCCGGTGGCGTCGGCGCTCACGCAGGGGCG
->RACE fragment 2
121         GGTCCCGGTAGCGCCAGGCGGTGCAGGGCGGGAAGGGGATTCGTGGCGACGGCGGCGGCA
181         AGGGACAGCAGGAGCAGTGGTGCTGTCAGCGCGGCCGTCGGAGACATGGGAGACCCGGGG
1                                                        M  G  D  P  G
241         TCGGAGATAATAGAATCTGTCCCTCCAGCTGGCCCTGAGGCATCTGAGTCAACAACGGAT
6            S  E  I  I  E  S  V  P  P  A  G  P  E  A  S  E  S  T  T  D
301         GAAAATGAAGACGACATTCAGTTTGTCAGTGAAGGACCATTACGACCTGTTCTTGAATAC
26           E  N  E  D  D  I  Q  F  V  S  E  G  P  L  R  P  V  L  E  Y
361         ATTGATCTGGTCAGCAGTGATGATGAAGAGCCTAGCACCTCTTATACTGATGAGAATATT
46           I  D  L  V  S  S  D  D  E  P  S  T  S  Y  T  D  E  N  I
421         AAACGTAAAGACCATATTGATTATCAGAAGGATAAGTTGCTTTAACTCTGGCTCGTCTA
66           K  R  K  D  H  I  D  Y  Q  K  D  K  V  A  L  T  L  A  R  L
481         GCCCGCCATGTTGAAGTGGAGAAACAGCAGAAAGAAGAGAAGAATAGAGCATTCAGAGAA
86           A  R  H  V  E  V  E  K  Q  Q  K  E  E  K  N  R  A  F  R  E
541         AAAATTGATTTTCAGCATGCTCATGGGTTACAAGAATTGGAATTTATTCGAGGACATTCT
106          K  I  D  F  Q  H  A  H  G  L  Q  E  L  E  F  I  R  G  H  S
601         GATACAGAAGCAGCAAGACTGTGTGTGGACCAGTGGCTAAAAATGCCAGGACTCAAAACA
126          D  T  E  A  A  R  L  C  V  D  Q  W  L  K  M  P  G  L  K  T
661         GGCACAATTAATTGTGGAACAAAAAGTTCATTCCGAAGAGGAGGCCACACGTGGGTGTCT
146          G  T  I  N  C  G  T  K  S  S  F  R  R  G  G  H  T  W  V  S
721         GGGAAACCAACTTTATGTCCTATAATGCACTGTAACAAGGAGTTTGACAATGGGCACCTT
166          G  K  P  T  L  C  P  I  M  H  C  N  K  E  F  D  N  G  H  L
781         CTCTTAGGACATTTGAAAAGGTTCGATCACTCTCCATGTGATCCAACAATTACACTACAT
186          L  L  G  H  L  K  R  F  D  H  S  P  C  D  P  T  I  T  L  H
841         GGACCTTTCTTCAGCTCCTTTGCTTGTGTAGTATGTTATAAAAAATTTGTTACTCAACAA
206          G  P  F  F  S  S  F  A  C  V  V  C  Y  K  K  F  V  T  Q  Q
901         CAATATAGAGATCACCTTTTTGATAAGGAAGCCACAGATGATGGACATAACAACAACCTT
226          Q  Y  R  D  H  L  F  D  K  E  A  T  D  D  G  H  N  N  N  L
961         CTTCCTCAGATTATTCAGTGTTTTGCATGTCCAAATTGCTTCCTTCTTTTTAGCAGAAAG
246          L  P  Q  I  I  Q  C  F  A  C  P  N  C  F  L  L  F  S  R  K
1021        GAGGAGTGTTCAAAGCATATGTCTGGAAAGAATCATTTCCATCAGAGTTTCAAACTGGGT
266          E  E  C  S  K  H  M  S  G  K  N  H  F  H  Q  S  F  K  L  G
1081        GATAACAAAGGAATTGCACATCCAATATCTTTCCCATCTTTTGCAAAGAAACTTTTGATC
286          D  N  K  G  I  A  H  P  I  S  F  P  S  F  A  K  K  L  L  I
1141        TCTCTGTGCAAAGATGTTCCCTTTCAAGTTAAGTGTGTGGCCTGCCACAAGACACTGCGT
306          S  L  C  K  D  V  P  F  Q  V  K  C  V  A  C  H  K  T  L  R
1201        TCCCACATGGAGCTCACTGCCCATTTCAGAGTTCATTGTCGAAATGCTGGACCTGTAGCT
326          S  H  M  E  L  T  A  H  F  R  V  H  C  R  N  A  G  P  V  A
1261        GTAGCTGAGAAGAGCATTACCCAGGTTGCAGAGAAATTCATATTAAGAGGTTATTGTCCA
346          V  A  E  K  S  I  T  Q  V  A  E  K  F  I  L  R  G  Y  C  P
1321        GATTGCAATCAAGTCTTTGTGGATGAAACCAGCACCCAAAATCATAAGCAGAATTCAGGA
366          D  C  N  Q  V  F  V  D  E  T  S  T  Q  N  H  K  Q  N  S  G
1381        CACAAAGTCCGAGTCATTAACTCAGTGGAAGAATCAGTCTTACTCTATTGCCACAGCAGC
386          H  K  V  R  V  I  N  S  V  E  E  S  V  L  L  Y  C  H  S  S
1441        GAAGGGAACAAGGATCCTTCTTCTGACTTGCATTTATTGTTGGATCAATCAAAATTTTCA
406          E  G  N  K  D  P  S  S  D  L  H  L  L  L  D  Q  S  K  F  S
1501        TCACTTAAAAGAACCATGTCTATTAAAGAATCTAGCTCACTGGAGTGCATTGCCATTCCA
426          S  L  K  R  T  M  S  I  K  E  S  S  S  L  E  C  I  A  I  P
1561        AAAAAGAAGATGAATTTAAAAGATAAAAGCCATGAAGGTGTTGCTTGTGTCCAGAAAGAA
446          K  K  K  M  N  L  K  D  K  S  H  E  G  V  A  C  V  Q  K  E
1621        AAATCAGTAGTTAAAACCTGGTTCTGTGAATGCAATCAGCGATTCCCAAGTGAAGATGCA
466          K  S  V  V  K  T  W  F  C  E  C  N  Q  R  F  P  S  E  D  A
1681        GTAGAAAAGCATGTTTTCTCAGCAAACACAATGGGTTATAAATGTGTGGTCTGTGGAAAG
486          V  E  K  H  V  F  S  A  N  T  M  G  Y  K  C  V  V  C  G  K
1741        GTATGTGATGATTCAGGGGTCATTCGTTTACACATGAGCCGGATTCACGGAGGGGCACAT
```

Figure 1 continued

```
506       V  C  D  D  S  G  V  I  R  L  H  M  S  R  I  H  G  G  A  H
1801      TTAAATAACTTTCTTTTCTGGTGTCGGACATGCAAAAAGGAGTTAACAAGGAAAGATACT
526       L  N  N  F  L  F  W  C  R  T  C  K  K  E  L  T  R  K  D  T
1861      ATCATGGCACATGTGACTGAATTTCATAATGGACACAGATATTTTTATGAGATGGATGAG
546       I  M  A  H  V  T  E  F  H  N  G  H  R  Y  F  Y  E  M  D  E
1921      GTAGAAGGTGAAACTTTGCCATCATCCTCTACAACATTGGATAATTTGACTGCTAACAAG
566       V  E  G  E  T  L  P  S  S  S  T  T  L  D  N  L  T  A  N  K
1981      CCTTCATCAGCTATTACTGTTATTGATCATTCCCCGGCAAATAGTTCTCCGAGGGGTAAA
586       P  S  S  A  I  T  V  I  D  H  S  P  A  N  S  S  P  R  G  K
2041      TGGCAATGCCGGATTTGTGAAGATATGTTTGATTCCCAGGAATATGTAAAACAGCACTGC
606       W  Q  C  R  I  C  E  D  M  F  D  S  Q  E  Y  V  K  Q  H  C
2101      ATGTCTTTGGCAAGCCACAAGTTTCATAGATACAGCTGTGCTCACTGCAGAAAGCCTTTT
626       M  S  L  A  S  H  K  F  H  R  Y  S  C  A  H  C  R  K  P  F
2161      CATAAGATAGAAACATTGTACCGACATTGCCAAGATGAGCATGACAATGAGATAAAGATT
646       H  K  I  E  T  L  Y  R  H  C  Q  D  E  H  D  N  E  I  K  I
2221      AAATACTTCTGTGGGCTTTGTGATCTTATCTTTAATGTGGAAGAAGCATTTCTGAGTCAT
666       K  Y  F  C  G  L  C  D  L  I  F  N  V  E  E  A  F  L  S  H
2281      TATGAGGAGCACCACAGCATAGATTATGTATTTGTGTCAGAAAAAACTGAAACTTCAATT
686       Y  E  E  H  H  S  I  D  Y  V  F  V  S  E  K  T  E  T  S  I
2341      AAAACCGAAGATGATTTTCCAGTAATAGAGACCAGTAACCAGTTAACTTGTGGTTGCCGT
706       K  T  E  D  D  F  P  V  I  E  T  S  N  Q  L  T  C  G  C  R
2401      GAGAGTTACATCTGTAAAGTCAACAGAAAAGAAGATTATAGCAGATGTCTCCAAATCATG
726       E  S  Y  I  C  K  V  N  R  K  E  D  Y  S  R  C  L  Q  I  M
2461      CTGGATAAAGGAAAACTGTGGTTTCGCTGCAGTTTATGTTCGGCAACAGCACAGAATTTA
746       L  D  K  G  K  L  W  F  R  C  S  L  C  S  A  T  A  Q  N  L
2521      ACCGACATGAACACTCATATCCATCAAGTGCACAAAGAAAAGAGTGATGAGGAGGAGCAG
766       T  D  M  N  T  H  I  H  Q  V  H  K  E  K  S  D  E  E  Q
2581      CAGTATGTAATCAAGTGTGGCACCTGCACCAAAGCATTTCATGATCCTGAGAGTGCACAG
786       Q  Y  V  I  K  C  G  T  C  T  K  A  F  H  D  P  E  S  A  Q
2641      CAGCATTTCCATAGAAAACATTGCTTCTTACAGAAACCCAGTGTGGCTCATTTTGGATCT
806       Q  H  F  H  R  K  H  C  F  L  Q  K  P  S  V  A  H  F  G  S
2701      GAAAAATCAAACCTGTACAAGTTTACTGCTAGTGCCTCACATACAGAGAGAAAACTGAAA
826       E  K  S  N  L  Y  K  F  T  A  S  A  S  H  T  E  R  K  L  K
2761      CAGGCAATAAACTATTCAAAAAGTTTAGACATGGAGAAAGGAGTTGAGAATGACCTAAGC
846       Q  A  I  N  Y  S  K  S  L  D  M  E  K  G  V  E  N  D  L  S
          TATCAGAATAT...
866       Y  Q  N  I...
``` splice variant: 144 base-pairs insertion (accession number AB011148)

```
          ...AGAGGAAGAAATTGTTGAGCTTCCAGATTTGGATTACCTGCGAACCATGACTCATATAGT
          ...E  E  E  I  V  E  L  P  D  L  D  Y  L  R  T  M  T  H  I  V
          CTTTGTAGATTTTGATAACTGGTCAAACTTTTTTGGTCATCTACCAGGGCATCTAAACCA
          F  V  D  F  D  N  W  S  N  F  F  G  H  L  P  G  H  L  N  Q
          AGGAACATTTATTTGGGGCTTTCA...
          G  T  F  I  W  G  F  Q...
2832      ...AGGAGGAAACACCAATTGGAAGCCTCCGCTCAACTGTAAGATTTATAAC
870       ...G  N  T  N  W  K  P  P  L  N  C  K  I  Y  N
2881      TACCTGAACAGGATTGGATGCTTCTTCCTTCATCCTCGCTGTAGTAAAAGAAAAGATGCT
886       Y  L  N  R  I  G  C  F  F  L  H  P  R  C  S  K  R  K  D  A
2941      GCTGATTTTGCCATATGTATGCATGCTGGCCGTCTAGATGAACAACTACCCAAGCAAATT
906       A  D  F  A  I  C  M  H  A  G  R  L  D  E  Q  L  P  K  Q  I
3001      CCTTTCACCATCCTCTCAGGAGATCAAGGTTTTCTGGAGCTAGAGAATCAATTTAAGAAG
926       P  F  T  I  L  S  G  D  Q  G  F  L  E  L  E  N  Q  F  K  K
3061      ACTCAGAGGCCAGCTCATATACTAAACCCTCACCACTTAGAGGGAGATATGATGTGTGCC
946       T  Q  R  P  A  H  I  L  N  P  H  H  L  E  G  D  M  M  C  A
3121      TTGTTAAATAGCATATCTGATACCACCAAAGAATGTGACAGTGATGATAACATGGGTGCC
966       L  L  N  S  I  S  D  T  T  K  E  C  D  S  D  D  N  M  G  A
3181      AAAAATACTTCAATAGGAGAAGAATTTATATCCACAGAAGATGTGGAATTAGAAGAAGCT
986       K  N  T  S  I  G  E  E  F  I  S  T  E  D  V  E  L  E  E  A
3241      ATTAGAAGAAGTCTTGAGGAAATGTAATTAAAGATATTACCACACAACATCAAGTGGCCT
1006      I  R  R  S  L  E  E  M
```

Figure 1 continued

```
3301    TGAAGAGACTGAGATAACGAATTCTTGAGTTTGTTTTCTAAAGGAGACCAGAAATCCACT
3361    ATTACAAATGTATTTGAAAACATGTTTTTGCTTTCATATGTTCAAAATTTGATCTTTGTT
3421    TTGTATTTTTGTGCTAATGTGCAAACATGTACAGAAGAAATAGAATACATGTTCATGCAA
3481    ATATAAATTATGTATTCTAATATAGGTGTAACAGTTTCCCAGTTAACTTTGAATTTATAT
3541    ATTTAGATTTAAAGGATTAAAAAAAAGGAAAGCTCTTGACAGTTGTTTCCCAAATAGCAT
3601    TAGTTCTTTAATTTTATTTGTACTGTACAAATGATGCTAGTTTATTTTTTTAGCAGTGAA
3661    AATGAATATAAAAAAGGTGACATAGGTCAAGTTTTCCATAAATTCTACTTCTCATGTGGC
3721    ACTATTATATAATACCTTTGAGATCTTTGTTTATGTTTATTAGAAGAGGGTAATGGAAAC
3781    TGATCATGGAAACATTTAAAATTTTATCAGCAATGTTCTTTGTGGGTGCCATGCATATGT
3841    AAATTATTGCTTTAATTAGAGCAGCACATTGCTAAAATAAAAAATACACCTTAATTTTTA
3901    AGAAATAATTTAAATGAAACAATTTCCATTCCTTTTACCTGCTTAGACTTTTATGTGACT
3961    TGTATGGTCTCCTGGTTAAAGGGAATGGTGTCAGAATATTTGCATAAAATTATTTTTCAT
4021    AACAGTCCTTTTTTATATATTGGTGTAAACATAATATTCTTCAAGAAATAATGTTGAAAG
4081    CCTACTCAGGAATAATCTTCCTTAACTCTTTAAATTTTTATTTCATGTGAAGTGTTTTCA
4141    GTTTAGTTATTCACTGAATTGTCAGTTTCCTTCATTTGGTATTACATATTTAATTCTTAA
4201    ATATTGAGGCCCCATTGTGAGTAATAAAAAATACGACATAAGTAGAAGACTAAGAAGGGC
4261    TTGTCATATTATCTTTGTGTATATGCTTCATGTTATTTAACCAGAAATGTCTTATCTCTA
4321    AAAATTTTAGTAGTAATTATTTACCAAACTTAAAAACATTTCTATAAATATAAAGCTTT
4381    TCTTTATATTTAAGACAAAATATAAAGGCTAGAATTTGGTTCCTTCTCTGTAACACTAAA
4441    TATTTTAGTGTGAAATTGAATTTTTTTATTACTATAGTCTTTTCAATCTATAATTTGTGT
4501    TTTTAATTTCTTGATATGTCACTTCTGTTCCTCCCTGCTTGCATTTTTAAAAACTAGAC
4561    ATTGTGGCTTGAGAATTTATCAATCATCTTTCCGAAATGACCACATTGTGCTTTTAGTTT
4621    GTATGTTTAAGTGGTCAAGCAAGGCTCTAGGAGGTAGTCACTGAGCTGGACCTTAAACAC
4681    ATCTGCAGGAGCTCACAAAATGGGAGCAAAAGAGGCATTCCAGAAAGAAGAGTAGTTAAG
4741    CAGATGTGGGGCAGGGCAAGAGGAGACAGCACCTTGTTGCCAGAGATTCTACACAAAGG
4801    TGTGATGGACACTGATGCTCTATTAAGAAGCTTTTGTGGTGTGTGTGGTAGAGAATAATT
4861    AAGGCTTCTGATAAGACAGGAAAGGGATATTTCATCATGACTGTTAAGAAAAGGTAACTG
4921    GGTTGTTTAATGTTTTAATTGATAATTGTCACTGATCGTATTTCTACTTGTTAAATAATT
4981    AAAAATCATCTTAAAATTC
```

COACTIVATION OF NUCLEAR RECEPTORS

This application is a national phase filing of PCT/EP01/09499, filed Aug. 16, 2001.

This application claims priority of European patent applications EPO 002029056, filed Aug. 21, 2000, and EPO 012017711, filed May 14, 2001.

FIELD OF THE INVENTION

This invention relates to a new protein, to an assay for binding between a responsive nuclear receptor and a coactivator and to a method of modulation of transcriptional activity promoted by a responsive nuclear receptor.

BACKGROUND OF THE INVENTION

This invention is in the field of the use of functions of nuclear receptors in organisms. Nuclear receptors have a wide range of function, but their most conspicuous role is to enable cells to respond to hormones, such as estradiol, cortisol, and progesterone. Via the nuclear receptors the hormones influence gene transcription in cells, whereby the cells can change their function. Furthermore, it is known that the activation of gene transcription by nuclear receptors is facilitated or even enabled by coactivators. Several such coactivators are known. For example, Nishikawa et al (Toxicol. Appl. Pharmacol. 154, pp 76-83, 1999) describe screening methods for chemicals with hormonal activities using the interaction of nuclear hormone receptors with a coactivator. Their method is based on the finding that the interaction between the coactivator and a nuclear receptor, which is responsive to that particular coactivator, can be stabilised by a ligand that binds to the nuclear receptor. Such assays are also important in order to unravel the action of hormones and mechanisms for control of transcription of genes in general. With these techniques new medicines can be developed in order to specifically influence physiological processes related to the functioning of nuclear receptors for therapeutic, diagnostic, cosmetic and contraceptive purposes.

SUMMARY OF THE INVENTION

This invention makes a protein available which has the amino acid sequence as given in SEQ ID's 7, 8, 11 or 12. Such a protein has the effect of coactivating a responsive nuclear receptor in its DNA-transcription promoting function.

With the finding of the function of such a protein as a coactivator this invention also provides a new method of modulation of transcriptional activity promoted by a responsive nuclear receptor and a coactivator in a system, comprising the addition of an agent to the system, which agent interferes with, or enhances, the function of the coactivator of this invention. This method can be performed both by introducing the gene for the coactivator in the system in order to bring it into expression as well as by identification and subsequent use of compounds which can change the functioning of the coactivator and/or the coactivator-nuclear receptor complex. Thus the term agent refers here, for example, to a chemical compound or to a vector, which vector comprises the gene encoding the protein of the invention. Such modulation can be used to interfere with, or to enhance, nuclear transcription processes for therapeutic, contraceptive, diagnostic and cosmetic purposes and it can be used in assays for quantification of the modulation. Thus, the term system refers to a molecularly and/or biologically defined environment and refers to in vitro systems as well as to in vivo systems in which the modulating agent can be introduced. In vitro systems are mixtures allowing DNA and/or RNA transcription/translation and in vivo systems are cells, which can be either in a cell or tissue culture or within a human or animal body. Obviously, the term modulation of the activity of a nuclear receptor can mean either an increase or a decrease in the transcriptional activity of the receptor, whereas the term coactivation means the enhancement of the transcriptional activity of the receptor.

DETAILED DESCRIPTION OF THE INVENTION

A sequence, putatively representing such a protein, is reported previously with gene number KIAA0576 in a publication by Nagase et al. (DNA Research vol 5, pp 31-39, 1998) by reference to accession number AB011148 for the EMBL/GenBank/DDBJ databases, where it is linked to protein_id BAA25502. The gene KIAA0576 was not made to expression beyond the RNA stage and no more specific function other than nucleic acid management was assumed based on a very weak homology (<30% identical nucleotides) to a known DNA sequence.

Since it is obvious that minor modifications in the sequence of the protein are equally useful for the above described use, the invention also provides for a protein having an amino acid sequence which has at least 90%, or preferably at least 95%, more preferably at least 99% and most preferably 100% similarity to the sequence in SEQ ID's 7, 8, 11 or 12. The term similarity refers to a degree of similarity between proteins in view of differences in amino acids, but which different amino acids are functionally similar in view of almost equal size, lipophilicity, acidity etc. A percent similarity can be calculated by optimal alignment of the sequences using a similarity scoring matrix such as the blosum62 matrix described in Henikoff and Henikoff (Proc. Natl. Acad. Sci. USA 89; 10915-10919 (1992)). Calculation of the percentage similarity and optimal alignment of two sequences using the blosum62 similarity matrix and the algorithm of Needleman and Wunsch (J. Mol. Biol. 48; 443-453 (1970)) can be performed using the GAP program of the Genetics Computer Group (GCG, Madison, Wis., USA) using the default parameters of the program.

It is a further aspect of the invention that the above described coactivating function can also be obtained with a protein having the sequence of amino acid number 1-234 in SEQ ID's 7 or 8. It is known that truncated proteins can have the same or partially the same function as the larger protein. It was found that this truncated protein can also be used and therefore this aspect of the invention also provides a protein having a sequence which has at least 90%, or preferably at least 95%, more preferably at least 99% and most preferably 100% similarity to the sequence of amino acid number 1-234 in SEQ ID's 7 or 8.

It is a further aspect of the invention to provide a protein which is a naturally occurring variant of a protein having the sequence as in SEQ ID's 7, 8, 11 or 12. Proteins which have at least 80% similarity, preferably at least 90%, more preferably at least 95%, even more preferably at least 99% and most preferably 100% similarity to the protein defined in SEQ ID's 7, 8, 11 or 12 and originating from human tissues or tissues of non-human species can likewise be used for coactivating a responsive nuclear receptor. Such polymorphic forms and species homologues are also included in the class of proteins made available by this invention. A naturally occurring protein belonging to the class defined by commonalities in the indicated structure and function of the protein defined by SEQ ID's 7, 8, 11 or 12, will be named by the arbitrary letter sequence COASTER proteins. In earlier documents, at least in documents having circulated within our research organisation the arbitrary letter sequence MFC has been used in order to provide a name for the proteins according to this invention. Thus, MFC and COASTER are synonyms. Other COASTER fragments also occur in biological tissue. Such fragments are encoded by splice variants.

Furthermore, having disclosed the structure of the protein and function of a COASTER protein, the invention also provides a protein which is a homologous functional equivalent of the protein as defined above. A homolous functional equivalent is a protein, which does not fullfill completely the earlier defined characteristics, because it has either less similarity than one of the above indicated percentages, or it is not the fragment as defined above, or it is of non-natural origin, but still has a characteristic function in common with the earlier defined proteins of the invention. For example, a fragment of a COASTER protein, can not only be used by itself for coactivation of the responsive nuclear receptor, but can also be fused with other protein sequences known from other proteins in order to take advantage of the nuclear receptor activating effect. Such fragments need not be 100% identical to the sequences of fragments of intact COASTER-proteins. Moreover, proteins functionally equivalent to COASTER proteins and splice variants thereof can be made artificially by deliberate mutations, insertions or deletions in the encoding poly-nucleotide sequence. A large degree of similarity of a protein with a protein specifically characterised in this description make a protein functionally equivalent to a COASTER protein. In this description a protein of this invention refers to any structurally similar or functionally equivalent artificial protein, splice variant or COASTER protein as defined above.

In view of the usefulness of the proteins, it is an aspect of the invention to provide the use of a polynucleotide encoding the protein of this invention by bringing the polynucleotide into expression in a system which also comprises a responsive nuclear receptor. The polynucleotide can either be a DNA or an RNA since both a DNA nucleotide sequence as well as an RNA sequence will serve the purpose of encoding the proteins of the invention. Preferred DNA's for use in this invention are the sequences given in SEQ ID's 1, 2, 3, 4, 5, 6, 9 or 10. Expression can be obtained by artificially incorporating the polynucleotide in eukaryotic cells, bacteria, plasmids or vectors and enabling transcription of the gene by methods generally known in the art. The system, which can be a mixture with components for DNA or RNA transcription and/or translation or an intact cell, possibly part of a whole organism, should also contain or generate the responsive nuclear receptor in order to be able to use the interaction between the protein of the invention and the nuclear receptor. A practical source of information on these techniques can be found in Sambrook et al., Molecular Cloning: a Laboratory Manual, Cold Spring Harbor laboratory Press, Cold Spring Harbor, 1989.

In the context of nucleotides one can also refer to degrees of similarity, whereby nucleotide triplets encoding the same amino acid can replace triplets in the above sequences. More common is to refer to homologous sequences of nucleotides: Homology of a polynucleotide is defined as:

$$\text{Homology (\%)} = \frac{\text{Number of identical residues between two sequences}}{\text{Length of aligned sequences} - \text{Length of all gaps}}$$

after optimal alignment of the sequences. Optimal alignment can be performed using the algorithm of Needleman and Wunsch (J. Mol. Biol. 48; 443-453 (1970)) that maximizes the number of matches and minimizes the number of gaps. In fact, a more restricted range of proteins can be defined by replacing the term similarity by homology having the analogous definition of homology of a polynucletide. Such a use of the term homology for a protein of the invention is based on the percentage identity of amino acid residues in the protein. Alternatively, the term degree of homology of a protein defined in this way, may also be replaced by the term degree of identity of a protein.

To accommodate codon variability, the invention also includes polynucleotide sequences coding for the same amino acid sequences as the sequences disclosed herein. The sequence information as provided herein should not be so narrowly construed as to require exclusion of erroneously identified bases. The specific sequence disclosed herein can readily be used to isolate the complete genes of several other species or allelic variants. The sequence can e.g. be used to prepare probes or as a source to prepare synthetic oligonucleotides to be used as primers in DNA amplification reactions allowing the isolation and identification of the complete variant genes. The complete genetic sequence can be used in the preparation of vector molecules for expression of the protein in suitable host cells.

The present invention further relates to polynucleotides having slight variations or having polymorphic sites. Polynucleotides having slight variations may encode variant polypeptides which retain the same biological function or activity as the natural, mature protein. Polymorphic sites are useful for diagnostic purposes.

In another aspect, the invention provides for a method to isolate a polynucleotide comprising the steps of: a) hybridizing a DNA according to the present invention under stringent conditions against nucleic acids being RNA, (genomic) DNA or cDNA isolated preferably from tissues which highly-express the polynucleotide of interest; and b) isolating said nucleic acids by methods known to a skilled person in the art. The tissues preferably are from human origin. Preferably ribonucleic acids are isolated from oocytes, ovaria or testes. The hybridization conditions are preferably highly stringent.

According to the present invention the term astringent means washing conditions of 1×SSC, 0.1% SDS at a temperature of 65° C.; highly stringent conditions refer to a reduction in SSC towards 0.3×SSC, more preferably to 0.1×SSC. Preferably the first two washings are subsequently carried out twice each during 15-30 minutes. If there is a need to wash under highly stringent conditions an additional wash with 0.1×SSC is performed once during 15 minutes. Hybridization can be performed e.g. overnight in 0.5M phosphate buffer pH 7.5/7% SDS at 65° C.

As an alternative the method to isolate the gene might comprise gene amplification methodology using primers derived from the nucleic acid according to the invention. Complete cDNAs might also be obtained by combining clones obtained by e.g. hybridization with e.g. RACE cDNA clones.

In order to use the modulation of transcription the system should also comprise genes for responsive nuclear receptors and responsive promoter elements for these nuclear receptors. The poly-nucleotide encoding a protein of this invention can be used for the production of recombinant COASTER protein to serve, in combination with a recombinant nuclear receptor protein, in an assay for binding of the protein with the responsive nuclear receptor.

The term responsive nuclear receptor is used in this description to refer to any nuclear receptor that can be activated by a COASTER-protein. Preferably the nuclear receptor in the system of the assay is a steroid receptor, or more preferably a progestogen receptor, an estrogen receptor or a glucocorticoid receptor.

A method of modulation of transcriptional activity promoted by a responsive nuclear receptor and a coactivator according to this invention can be an in vitro assay for determination of the degree of modulation and comprises quantifying the degree of modulation. Provisions for quantification of the degree of modulation or binding may comprise a yeast two-hybrid assay such as described here or an analogous two-hybrid assay in a mammalian cell system. Alternatively, the binding efficiency may be measured using isolated recombinant proteins of COASTER and the nuclear receptor that are suitably labelled to allow detection of the binding efficiency. Labelling of the proteins may involve radioactive or fluorescent molecules or molecules with enzymatic properties that are directly or indirectly attached to the recombinant proteins. Alternatively, the binding efficiency may be measured by an affinity based biosensor system such as the BIACORE. Alternatively, the binding efficiency might be measured by in vitro or in vivo complementation assays that use the interaction of COASTER protein and the nuclear receptor to drive complementation of a functional protein, such as β-galactosidase or dihydrofolate reductase, whereby the function of the complemented protein is used as a measure for the binding efficiency.

The method of modulation of transcriptional activity promoted by a responsive nuclear receptor and a coactivator according to this invention can also be a treatment of the human or animal body comprising the administration of the agent to the human or animal. Such an agent can be a vector inserting the gene for the coactivator into cells of the organism thereby enabling production of more coactivator for activation of the nuclear receptor or it can be a vector inserting a gene for a defective coactivator into cells of the organism thereby enabling production of a protein according to the invention which interferes with the action of the endogenous COASTER protein, resulting in diminished action of the nuclear receptor. The agent can also be a chemical compound which influences the interaction between the coactivator and the responsive nuclear receptor. Such a compound can be obtained by routine screening in an assay for binding between the coactivator and the responsive nuclear receptor or in an assay for quantification of the modulation of the action of the responsive nuclear receptor.

It is therefore a further aspect of the invention that the assay or method according to the invention can be used to select compounds which modulate the binding between a COASTER protein and a responsive nuclear receptor, or which modulate the activity of a nuclear receptor-COASTER complex. In such an assay, compounds are being tested for their ability to induce or perturb an interaction between COASTER and a responsive nuclear receptor, or, alternatively, upon their ability to modulate transcription via a responsive nuclear receptor and in the presence of COASTER and a reporter DNA.

A reporter DNA consists of a promoter that is responsive to the nuclear receptor under study, and a reporter gene whose transcriptional activity can be monitored. The promoter may either be an isolated natural promoter of a nuclear receptor-responsive gene, or a synthetic cassette of (multiple copies on a consensus nuclear receptor responsive element fused to a basal core promoter (e.g. a TATA box). Suitable reporter genes include genes that encode enzymes whose activity can be monitored via an enzymatic assay (e.g. luciferase or β-galactosidase), genes that encode proteins with fluorescent properties (e.g. Green Fluorescent Protein), or genes whose transcripts levels can be monitored.

The latter assay is particularly advantageous because COASTER potentiates the action of an estrogen-receptor-responsive element (ERE) containing promoter in the presence of the estrogen receptor a and a partial agonist, thereby enabling the identification of novel partial agonists. Known ERE-based assays are not able to recognize all partial agonists (e.g. raloxifen).

The invention also provides a pharmaceutical composition as a medicine for the mentioned method of modulation of transcriptional activity promoted by a responsive nuclear receptor and a coactivator in a system, comprising the administration of an agent to a human or animal body, which agent interferes with, or enhances, the function of the coactivator of this invention. This the invention also provides a pharmaceutical composition for use in the mentioned, which pharmaceutical composition comprises the agent which interferes with, or enhances, the function of the coactivator. As explained above a compound identified with the assays provided by the invention can interfere with, or enhance, the function as coactivator of the protein of the invention. Alternatively, a vector comprising the gene for a protein according to the invention can be formulated for medicinal use.

A method of preparation of a medicine by mixing the agent with one or more pharmaceutically acceptable auxiliaries such as described in the standard reference Gennaro et al., *Remmington's Pharmaceutical Sciences*, (18th ed., Mack publishing Company, 1990, see especially Part 8: Pharmaceutical Preparations and Their Manufacture.) is well known in the art. Suitable auxiliaries are described in e.g. the Handbook of Pharmaceutical Excipients ($2^{nd}$ Edition, Editors A. Wade and P J. Weller; American Pharmaceutical Association; Washington; The Pharmaceutical Press; London, 1994). The mixture of the agent and the pharmaceutically acceptable auxliary may be compressed into solid dosage units, such as pills, tablets, or be processed into capsules or suppositories. By means of pharmaceutically suitable liquids the agent can also be applied as an injection preparation in the form of a solution, suspension, emulsion, or as a spray, e.g. nasal spray. For making dosage units, e.g. tablets, the use of conventional additives such as fillers, colorants, polymeric binders and the like is contemplated.

Such pharmaceutical compositions can be used in a COASTER-activated nuclear receptor related treatment, more specifically against hormone stimulated tumor growth, for male or female contraception, for the treatment of menopausal complaints and post-menopausal disorders in women, for anabolic drug treatment, for heart diseases and for the treatment of aging due to reduced hormonal activity.

Since the COASTER protein displays a tissue-specific expression profile, such medicines may contribute to tissue-specific treatments. Moreover, the presence or modulation of COASTER may alter the pharmacology of nuclear receptor ligands. For example, raloxifen is usually an antagonist, but when COASTER is clearly expressed in the cell, raloxifen displays agonistic properties.

Properly labelled poly-nucleotides having a sequence encoding proteins for the invention or fragments thereof are also made available by this invention. These can be used in methods of diagnosis by stringent quantitative hybridisation of RNA in order to identify diseases related to abnormal expression of COASTER-RNA in an organism. These methods can advantageously involve the use of such a labelled poly-nucleotide having a length of at least 500 nucleotides, in order to have accurate identification of RNA with hybridisation. However a length of between 20 and 50 nucleotides can also be preferred as being more practical and still effective for this purpose. For diagnostic purposes, expression of the COASTER mRNA can also be detected by nucleotide chain reaction, such as reverse-transcriptase polymerase chain reaction (RT-PCR). To this end, cDNA is synthesized from RNA isolated from a sample specimen using a reverse transcriptase enzyme. The cDNA is subsequently used as a template in a polymerase chain reaction in the presence of a COASTER antisense and sense oligonucleotide primer. The amount of amplified PCR product, that can be determined by isotopic or non-isotopic labeling in combination with appropriate detection methods or by direct spectrophotometric or calorimetric methods, reflects the relative expression level of the COASTER mRNA.

Labelling can be done in various ways. In the case of radioactive labelling, hybridisation of poly-nucleotides may be measured by quantitation of the number of desintegrations per second of the radiolabeled hybrid. Alternatively, hybridised radiolabeled fragments may be visualized by autoradiography or similar methods. Non-isotopic labelling methods often make use of biotinylated nucleotides that are incorporated during labelling of the fragment. Successfully hybridised fragment can subsequently be detected by virtue of the incorporated biotin. The biotin moiety can be detected using an avidin molecule conjugated to a molecule with fluorescent or enzymatic properties. The amount of fluorescence or enzymatic activity is used as a measure for the hybridisation efficiency.

The diagnostic method will be particularly useful for diseases involving tumour growth. It is striking that the COASTER gene is strongly expressed in tumor cell lines. The diagnostic method can be performed by scanning or taking biopsies from the organism to be diagnosed, but the method can be strictly limited to a method which is not practised on the human or animal body. In that situation the method comprises in vitro testing of available biological material for hybridisation. In view of the sensitivity of the nuclear receptors for COASTER the method is preferrably to be used when the suspected disease relates to malfunction of a steroid receptor, or more preferrably with a progestogen receptor, an estrogen receptor or a glucocorticoid receptor.

The proteins for the invention can also be used to produce anti-bodies directed to these proteins, which antibodies can be used in diagnostic methods of disorders involving changes in the coactivation process disclosed in this invention.

Methods for the production of monoclonal and polyclonal antibodies can be found in a standard laboratory manual such as Current Protocols in Molecular Biology (F M. Ausubel, R. Brent, R E. Kingston, D. D. Moore, J G. Seidman, J A. Smith, K. Struhl eds., John Wiley & Sons Inc.). Immunisation may be performed using crude or purified preparations of COASTER protein or via DNA vaccination using a mammalian expression vector for COASTER that is directly used to immunise the antibody donor organism.

Poly-nucleotides encoding COASTER artificially incorporated in eukaryotic cells, bacteria, plasmids or vectors and COASTER protein can be obtained by amplification by a polymerase chain reaction on a cDNA template that has been obtained by reverse transcription of RNA from human testis. The polymerase chain reaction should make use of a sense primer encompassing the start codon of the COASTER cDNA (e.g. ATGGGAGACCCGGGGTCGGA; SEQ ID 13) and an antisense primer encompassing the stop codon of the COASTER cDNA (e.g. TTACATTTCCTCAAGACTTC; SEQ ID 14). Cloning of the thus obtained cDNA in a suitable expression vector will allow production of the COASTER protein.

By deletions and insertions of nucleotides partially identical artificial COASTER proteins can be obtained with methods well known to the skilled person, for example as described in Sambrook (op. cit.).

The COASTER protein may be introduced into an organism by transfection of an expression vector containing the COASTER cDNA. The vector should contain a promoter that is able to drive gene expression in the transfected organism, and the COASTER cDNA downstream of this promoter. In addition, the vector should contain signals for proper initiation and termination of transcription and translation, and signals for proper processing of the transcript. For introduction of COASTER in mammalian cells viral promoters such as the Simian Virus 40, Rous Sarcoma long terminal repeat or Cytomegalovirus immediate early promoters are suitable for driving transcription of the COASTER cDNA. Examples of plasmid vectors containing viral promoters include pCDNA3.1, pRSV and pNGV1. In addition to introduction of COASTER into mammalian cells with the aid of plasmids, COASTER may be introduced into mammalian cells by transduction using viral vehicles for delivery and expression of COASTER. Suitable viruses include retroviruses, adenoviruses and baculovirus.

For introduction of COASTER in bacterial cells vectors containing bacterial promoters such as the T7 promoter are suitable. Examples of bacterial expression vectors include pRSET and pET. For introduction of COASTER in yeast, suitable vectors include pYES for introduction in *Saccharomyces cerevisiae* and pPIC for introduction in *Pichia pastoris*.

A straightforward method is available to select a responsive nuclear receptor for the assay. For example, it can be tested whether a nuclear receptor is coactivated by COASTER protein in a transient transfection assay. When there is coactivation, the nuclear receptor is responsive. The action of a nuclear receptor is the induction of transcription of a gene linked down stream to a promoter. With a two-hybrid assay, for example, it can be tested whether the nuclear receptor interacts with the COASTER protein.

Likewise, the functional equivalence to COASTER protein of an artificial protein can routinely be tested in an assay as described in the examples.

The following description of variants and use of the invention is intended to further enable the invention and the use of it.

Coactivation of the Selective Estrogen Receptor Modulator (SERM) Liganded ERα Depends on the AF1 Region.

FIG. 4 shows that COASTER is a coactivator for the 4OH-tamoxifen liganded ERα but not for the 4OH-tamoxifen liganded ERβ. These results are in good agreement with previous observations that the SERM 4OH-tamoxifen signals via the AF1 function of ERα. The AF1 function resides in the AB domain of the ERα and is neither structurally nor functionally conserved in ERβ (McInerney et al., 1998, Endocrinology 139, 4513-4522). To substantiate this notion, we tested the coactivating potential of COASTER on two receptor chimeras. The ERβ/α, chimera contains the AB domain of ERβ fused to the CDEF domains of ERα as described previously (McInerney et al., 1998, Endocrinology 139, 4513-4522). In transfection experiments the ERβ/α receptor permits coactivation by COASTER in the presence of 17β-estradiol, but not in the presence of the SERMs 4OH-tamoxifen and raloxifene (FIG. 8). This observation indicates that coactivation by COASTER of the SERM liganded receptor is distinct from coactivation of the 17β-estradiol liganded receptor. In line with the previous observation that signalling by 4OH-tamoxifen requires the ERα AF1, our results show that 4OH-tamoxifen does not display agonism on the ERβ/α chimera. Furthermore, our data show that elevating the COASTER levels in the cell cannot overcome this block in activity, indicating that coactivation of the SERM liganded receptor requires the ERα AF1. The situation on the ERα/β chimera, which contains the ERα AF1 fused to the CDEF domains of ERβ, is more complex. It has been shown previously that the ERα/β chimera shows agonism of 4OH-tamoxifen and an activity in the presence of 17β-estradiol that is reduced compared to that of the wild type ERα or ERβ receptors (McInerney et al., 1998, Endocrinology 139, 4513-4522). Our data confirm and extend these results and show that in addition to 4OH-tamoxifen and 17β-estradiol, raloxifene is also able to signal via the ERα/β chimera. However, the ERα/β chimera is insensitive to coactivation by COASTER. The combined results indicate that the ERα/β chimera adapts a unique conformation and suggest that the coactivation as seen on the 17β-estradiol-liganded wild type ERβ depends on both the AF2 function and sequences in the N-terminus of ERβ.

COASTER Identifies Novel SERMs

The results presented in FIGS. 4 and 5 show that in the absence of COASTER, 4OH-tamoxifen may function as an agonist on ERα whereas raloxifene may not. Elevation of the COASTER levels in the cell allows the identification of raloxifene as a ligand with agonistic potential. We questioned whether COASTER would allow the identification of novel potential SERMs in a pool of compounds that have previously been identified as anti-estrogens. To this end, we tested the activities of the compounds ORG 43143, ORG 39660 and ORG 39669 that were identified as novel anti-estrogens in a high throughput screening assay (Method in Dechering et al., 2000, Current Medicinal Chemistry 7, 561-576). FIG. 9 shows that these compounds all behave as anti-estrogens. Notably, compound ORG 39669 shows a partial activity in the anti-estrogenic assay. When tested in a COASTER co-activation assay, this group of anti-estrogens falls apart into three distinct functional classes (FIG. 10). The first class comprises 4OH-tamoxifen and ORG 39669 and represents a group of compounds that show some agonism on ERα and enhanced agonism in the presence of COASTER. The second class is a group of anti-estrogens that are silent on ERα mediated transcription of an ERE reporter in the absence of COASTER. However, when COASTER levels are elevated, these compounds become agonists. The compounds raloxifene and the novel anti-estrogen ORG 43143 are representatives of this second class. The final class of anti-estrogens includes ICI 164,384 and ORG 39660 and represents a group of compounds that do not show agonism on an ERE reporter and remain silent in the presence of COASTER.

Tissue Distribution of COASTER

The tissue distribution of COASTER mRNA was investigated by Northern blot analysis and RT-PCR. Human multiple tissue Northern blots were hybridized with a 794 bp COASTER cDNA fragment. Almost all tissues examined show hybridisation to an mRNA species of approximately 5 kB in size, with higher signals in testis, ovary, heart, placenta, and skeletal muscle, and lower to no signals in the other tissues (FIG. 6). In addition, a very strong hybridisation signal is observed to a 4 kB transcript that is uniquely present in testis. The size of the 5 kB transcript is in good agreement with the size of the cDNA that we have isolated. The 4 kB transcript may represent a splice-variant. The testis specific expression pattern of this transcript is striking and suggests a functional role in testis physiology.

Expression of mRNA from COASTER was also investigated by RT-PCR analysis in different human cell lines derived from tumors, and in RNA samples from human and *Macaca fasciculata* (Cynomolgus monkey) tissues. The semi-quantitative results of the RT-PCR are shown in FIGS. 7 and 11. The results show high expression in the breast epithelial carcinoma cell lines MCF-7 and T-47 and the vaginal epithelial cell line SW954. Moderate expression was observed in the osteosarcoma cell lines U-2 OS and HOS, the endometrial epithelial carcinoma cell line Ishikawa, the vascular endothelial cell line VE103ERα, and the endothelial cell line HS760T. No expression was detected in the osteosarcoma cell line MG63 and the endometrial epithelial carcinoma cell line ECC-1. The cell lines that show high expression of COASTER (MCF-7, T-47D, SW954) have been reported to contain high levels of ERα (Dechering et al., Curr. Med. Chem. 7, 561-576), suggesting that COASTER may contribute to ERα-mediated growth of tumor cells. The RT-PCR results on RNA derived from tissues are presented in FIG. 11. The RT-PCR method confirms the high expression in testis as revealed by the Northern blot (FIG. 6). In addition, high expression is seen in bone tissue. This indicates that ligands that allow the nuclear receptor-COASTER interaction might influence bone metabolism.

BRIEF DESCRIPTION OF THE FIGURES

Further examples and figures serve to illustrate and clarify or specify the invention.

The description is illustrated with the following figures:

FIG. 1. Example of a nucleotide and amino acid sequence of COASTER. This COASTER cDNA sequence has a length of 4999 base-pairs with an open reading frame of 3039 base-pairs (1013 amino acids). A previously published sequence of the cDNA encoding KIAA0576 (accession number AB01148) with near complete homology (99%) shows an insertion of 144 nucleotides at position 2832 that results in an open reading frame of 1061 amino acids. Zinc finger motifs are shown in bold, an LXXLL motif is underlined. The amino acid sequence of a consensus nuclear localisation signal is shown in italics and underlined. The ATG start codon and in-frame translational stop codons are shown in bold and italics.

EXAMPLES

Figure 2:
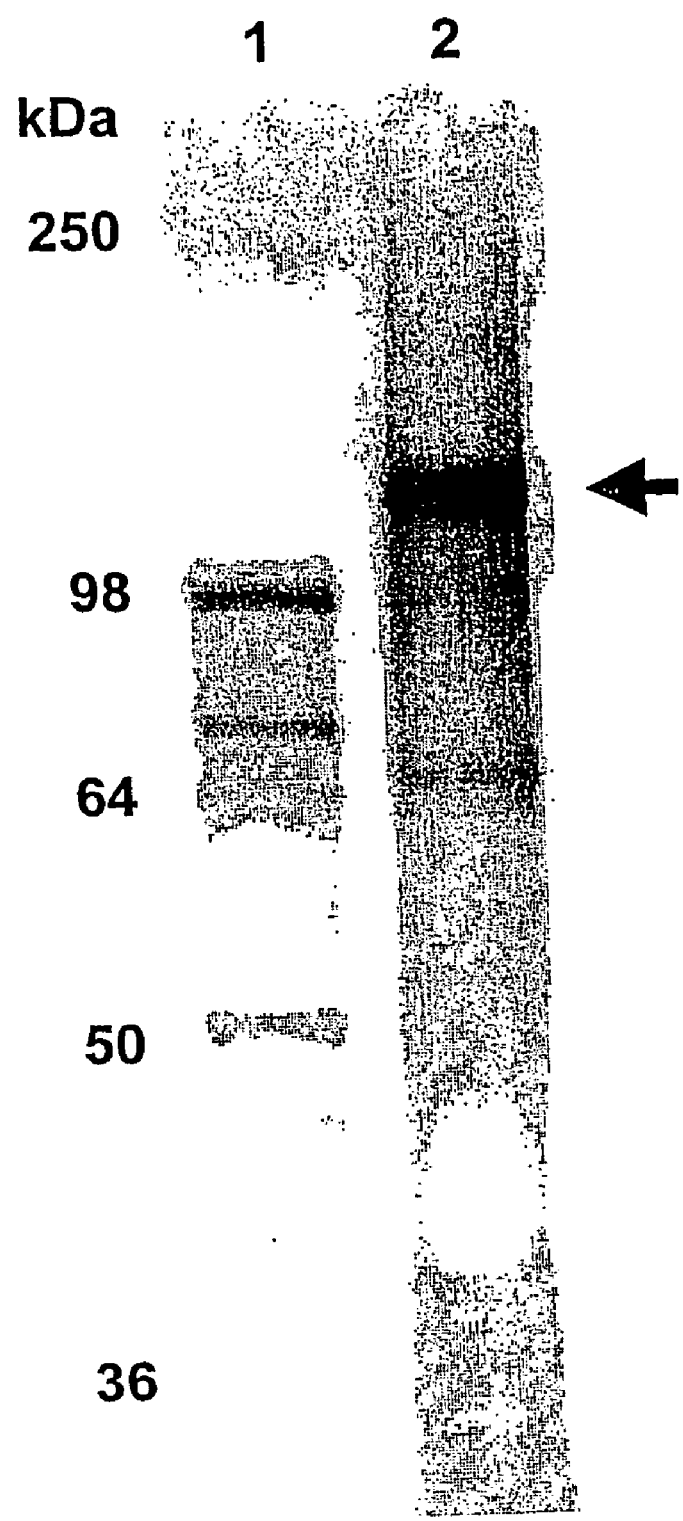
FIG. 2. The COASTER cDNA sequence encodes a protein of approximately 115 kiloDaltons. Template pCDNA3.1HISC.COASTER that contains the complete open reading frame of COASTER was in vitro transcribed and translated in the presence of [$^{35}$S]-methionine. As a control, pBK-SRC-1 (Onate et al., Science 270, 1354-1357) was transcribed and translated in parallel. Labeled proteins were analyzed by SDS-PAGE. The figure shows an autoradiograph of the electrophoresis pattern. Lane 1: translation product of pBK-SRC-1. Lane 2: translation product of pCDNA3.1HISC.COASTER. The position of the COASTER protein is indicated with an arrow.

Identification of a Novel Coactivator for Steroid Receptors

Results and Discussion

Yeast Two Hybrid Screen

For identification of COASTER as protein that interacts with ERβ in a hormone dependent way, a yeast two-hybrid screen was performed using ERβ as bait. The two-hybrid system consisted of a yeast strain (AH109) that expressed the HIS3, MEL1, ADE2 and lacZ reporter genes from a GAL responsive promoter. ERβ was expressed in this strain in a fusion with a GAL4 DNA binding domain. In this system, ERβ alone is not able to activate the reporter genes in the presence of 17β-estradiol (results not shown). The ERβ expressing host strain was transformed with a human osteosarcoma cDNA library. This library expresses cDNA as a translational fusion with a GAL4 transactivating domain. Interaction between ERβ and a library encoded protein permits activation of the reporter genes and growth on media lacking histidine and/or adenine. A total of $3.5 \times 10^6$ colonies were screened. The transformed yeast cells were selected for growth on media lacking histidine and in the presence of 17-β estradiol. 560 HIS$^+$ colonies were selected and screened by replica plating on their ADE$^+$ phenotype in the absence or presence of 17-β estradiol. 27 Yeast transformants that showed a hormone dependent HIS$^+$, ADE$^+$ phenotype were selected. The library-derived plasmid DNA was isolated from these 27 clones, and re-introduced in the AH109.pGBT9.ERβ host yeast strain to verify that the observed phenotypes were dependent on the transformed DNA. In a yeast β-galactosidase (lacZ transactivation assay, 21 out of the 27 positives that were retested showed a hormone inducible lacZ$^+$ phenotype. Sequence analysis of these positives identified two well-known coactivators for steroid receptors, UBC9 (ubiquitin conjugating enzyme) and SUG1. In addition, a cDNA sequence was identified that was predicted to encode for a nuclear protein with several zinc finger motifs and an LXXLL domain, which apparently is implicated in the interaction between steroid receptors and coactivators. This cDNA was selected for further study and proved to encode a functional coactivator for steroid receptors. We have, therefore, termed this novel coactivator COASTER.

COASTER: A Novel Coactivator for Steroid Receptors

Primary Structure of COASTER

The insert of plasmid pACT2.COASTERΔ that was isolated in the two-hybrid screen was sequenced, and this sequence was compared with the Incyte Lifeseq Gold and Genbank databases using the BLAST algorithm. A total of 270 Incyte EST sequences were identified. Clone 2905757, containing the 3' end of the COASTER cDNA, was obtained from Incyte Genomics (Palo Alto, USA) and sequenced entirely. In addition, searching of the Genbank database revealed that the COASTER sequence shares near complete homology (99%) with the gene encoding KIAA0576, a putative protein of unknown function (Nagase et al., DNA Res. 5, 31-39). The KIAA0576 sequence represents a splice-variant of COASTER and contains an in-frame insertion of 144 base pairs. RACE PCR was employed to identify the 5' end of the COASTER cDNA sequence. Two distinct fragments that differ in their 5' untranslated regions were identified. FIG. 1 shows an overview of the complete COASTER cDNA sequence. The cDNA corresponding with the longest RACE fragment has a length of 4099 nucleotides and contains an open reading frame of 3039 nucleotides (1013 amino acids). The KIAA0576 shows an insertion of 144 nucleotides at position 2832 that results in an open reading frame of 1061 amino acids. For both COASTER and KIAA0576, the amino acid sequence deduced from the cDNA predicts a protein that contains 9 zinc finger domains ($C_2H_2$ type), a nuclear localization site and an LXXLL nuclear receptor interaction motif.

The COASTER cDNA Encodes a Protein

To test whether the COASTER cDNA indeed encoded a protein, plasmid pCDNA3.1HISC.COASTER that contains the complete open reading frame of COASTER (amino acids 1-1013) was in vitro transcribed and translated. FIG. 2 shows that a protein of approximately 115 kiloDaltons is encoded by the COASTER cDNA. The observed size of the protein is in perfect agreement with the length of the cDNA sequence presented in FIG. 1. The results furthermore show that the COASTER cDNA encodes a protein that is distinct from the protein encoded by pBK-SRC-1, which contains the open reading frame for the known coactivator SRC-1.

COASTER Interacts with ERβ in Yeast

Figure 3:
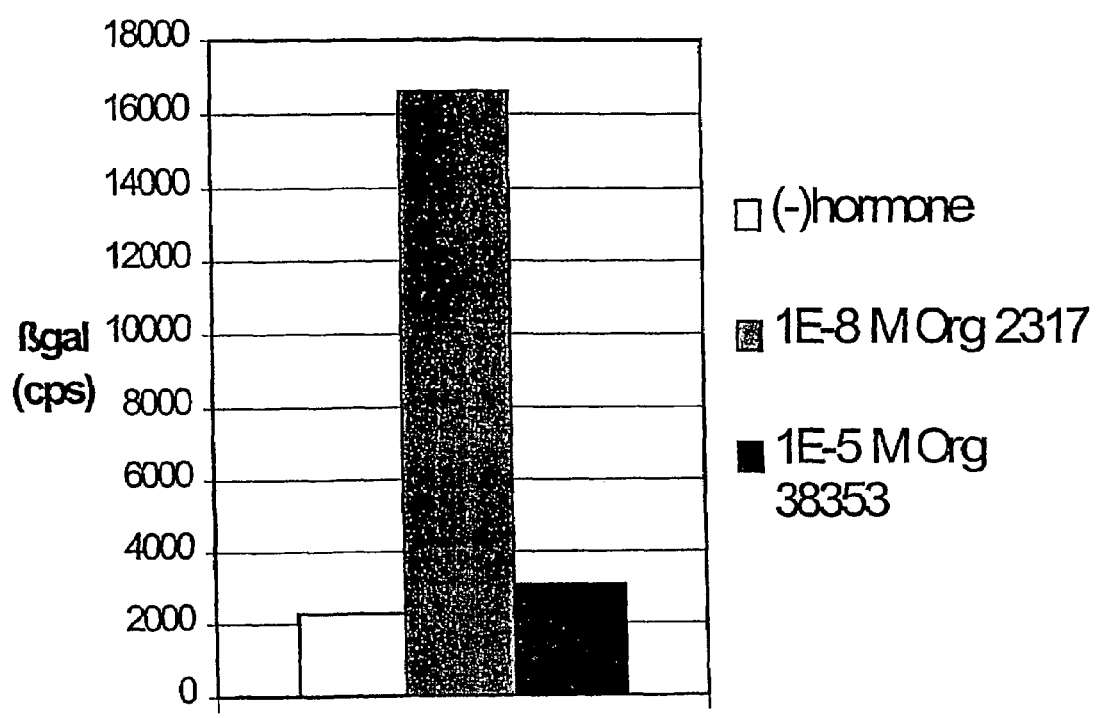
FIG. 3. Hormone dependent interaction between ERβ and COASTER. A yeast two-hybrid assay was performed in yeast host Strain AH109 that was transformed with plasmid pGBT9. ERβ and a plasmid encoding a fusion between a GAL4 activation domain and COASTER amino acids 1-234. The figure shows β-galactosidase activity of the transformed yeast cells in response to $10^{-8}$ M 17β-estradiol (shaded bar) and $10^{-5}$ M raloxifen (solid bar). The background β-galactosidase activity of the transformed yeast cells is indicated with an open bar.

Plasmid pACT2.COASTERΔ was originally isolated in the yeast two-hybrid screen. To verify that the protein encoded by this plasmid indeed interacts with ERβ in yeast, plasmid pACT2.COASTERΔ was re-introduced into the AH109.pGBT9.ERβ recipient strain. FIG. 3 shows the results of a subsequent two-hybrid assay. The results show that addition of 17β-estradiol to the growth medium results in a dose-dependent induction of the β-galactosidase reporter activity. In contrast, the anti-estrogens raloxifen is not able to induce the activity of the reporter. This failure may relate to the resistance of yeast cell to anti-estrogens as has been reported earlier (Lyttle et al., J Steroid Biochem. Biol. 42, 677-685; IH, unpublished results). Alternatively, it may indicate that the anti estrogen induced conformation of ERβ does not permit an interaction with COASTER. Transformation of the yeast strain with either the ERβ expression plasmid or the COASTER expression plasmid alone did not result in a 17β-estradiol inducible lacZ⁺ phenotype (data not shown). Together, the results indicate that ERβ and COASTER interact in a 17β-estradiol-dependent manner in yeast. The interaction is independent of the LXXLL motif of COASTER as this motif is not encoded by plasmid pACT2.COASTERΔ that was used in the yeast two-hybrid assay.

COASTER is a Functional Coactivator in Mammalian Cells

To test the functional role of COASTER in a mammalian setting, the full length COASTER (amino acids 1-1013) cDNA was cloned in a mammalian cell expression vector. The functional role of COASTER was analyzed by cotransfection of U-2 OS cells with the COASTER expression plasmid in combination with a steroid receptor expressing plasmid, and a plasmid containing a luciferase reporter gene under control of a hormone responsive element. Following transfection, cells were stimulated with the appropriate hormone for the receptor under study. The results are presented in Table 1:

TABLE 1

| T st cells | | no hormone | $10^{-8}$ M ICI 164,384 |
|---|---|---|---|
| | | $10^{-8}$ M 17β-estradiol | |
| 1 | Erβ | 150 ± 14 | 500 ± 109 | 134 ± 28 |
| | ERβ + COASTER | 133 ± 16 | 8200 ± 819 | 101 ± 6 |
| 2 | ERα | 180 ± 22 | 9505 ± 2122 | 174 ± 18 |
| | ERα + COASTER | 134 ± 18 | 15400 ± 1179 | 275 ± 55 |
| | | $10^{-8}$ M Org 2058 | |
| 3 | PR | 62 ± 22 | 822 ± 112 |
| | PR + COASTER | 81 ± 48 | 3229 ± 683 |
| | | $10^{-8}$ M Dexamethasone | |
| 4 | GR | 44 ± 3 | 1232 ± 82 |
| | GR + COASTER | 103 ± 33 | 35245 ± 8679 |

Legend to Table 1: COASTER is a coactivator for steroid receptors. U-2 OS cells were transiently transfected with pNGV1.ERβ and p4ERE-TATA-LUC (1), pNGV1.ERα and p4ERE-TATA-LUC (2), pKCRE.PR and pMMTV-LUC (3) or pNGV1.GR and pMMTV-LUC (4). Where indicated, COASTER expression construct pCDNA3.1HISC.COASTER was added to the transfection mixture. Following transfection, cell were incubated with the hormones indicated in the top row. The table shows luciferase activities± standard deviations from a triplicate experiment. Org 2058=16α-ethyl-21-hydroxy-19-norpregn-4-ene-3,20-dione.

As can be seen in table 1, COASTER is a coactivator for the progesterone receptor (PR), glucocorticoid receptor (GR) and the estrogen receptors α and β (ERα and ERβ). In all cases, the activity of the receptor liganded with an agonist is further enhanced by co-expression of COASTER. When ERα or ERβ are liganded with the antagonist ICI164,384, co-expression of COASTER does not enhance the transcriptional activity, indicating that the antagonist induced conformation does not allow COASTER to function as a coactivator. The activity of the reporter gene was not induced when COASTER was transfected in the absence of a steroid receptor (data not shown), indicating that both the steroid receptor and COASTER are required for the enhanced activity.

COASTER Identifies Partial Agonists for the Estrogen Receptor α

Figure 4:
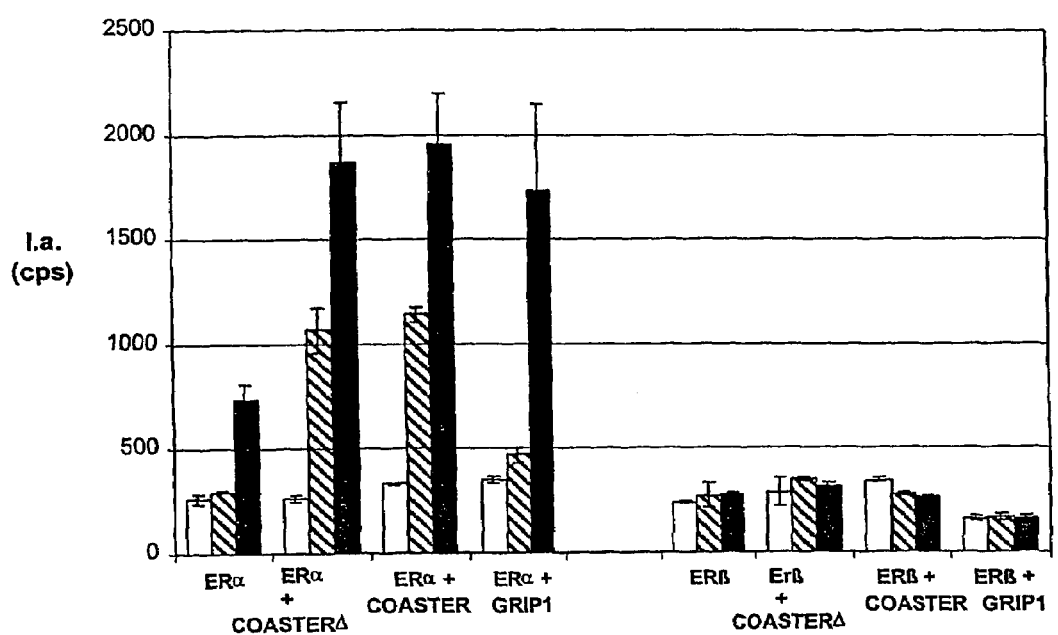
FIG. 4. Differential coactivation of ERα and ERβ in response to 4OH-tamoxifen and raloxifen. U-2 OS cells were transiently transfected with p4ERE-TATA-LUC and pNGV1.ERα or pNGV1ERβ as indicated. Where indicated, cells were cotransfected with COASTER expression constructs pCDNA3.1HISA.COASTERΔ or pCDNA3.1HISC.COASTER, or with expression construct pCDNA3.1HISC.GRIP1. The figure shows luciferase activity (l.a.) following incubation of the cells with no hormone (open bars), $10^{-7}$ M raloxifen (hatched bars) or $10^{-7}$ M 4OH-tamoxifen (solid bars). Error bars indicate the standard deviations in a triplicate experiment.
Figure 5:
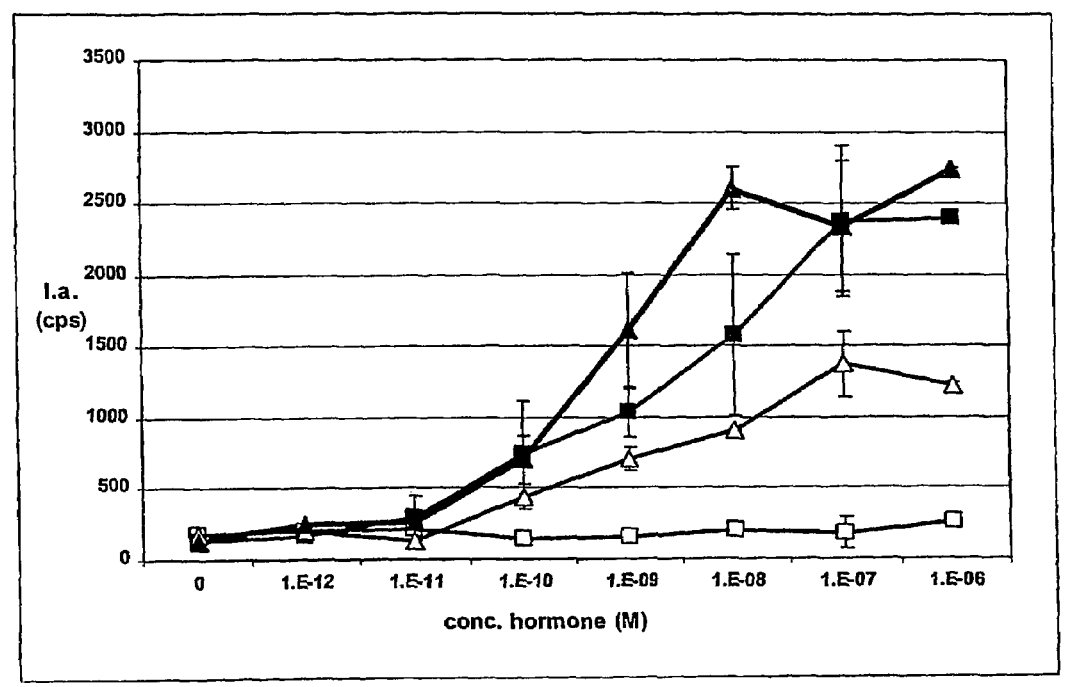
FIG. 5. Dose-dependent activation of an estrogen-response element in the presence of ERα or ERα in combination with COASTER. U-2 OS cells were transiently transfected with p4ERE-TATA-LUC and pNGV1.ERα. Transfection experiments indicated with solid markers were supplemented with COASTER expression construct pCDNA3.1HISC.COASTER. The figure shows luciferase activity (l.a.) following incubation of the cells with an increasing concentration of raloxifen (indicated with squares) or 4OH-tamoxifen (indicated with triangles). Error bars indicate the standard deviations in a triplicate experiment.

The coactivating potential of COASTER on ERα and ERβ was further studied in the presence of the anti-estrogens raloxifen and 4OH-tamoxifen. For comparison, the activity of the coactivator GRIP1, which is the mouse orthologue of human TIF2/SRC-2, was analyzed in parallel. Transfection-experiments showed that in U-2 OS cells, 4OH-tamoxifen acts as an agonist on the transcriptional activity of ERα, but not ERβ, when an ERE-reporter is used as a read-out (FIG. 4). Cotransfection of either COASTER or GRIP1 results in an enhanced activity of the 4OH-tamoxifen-liganded ERα. Interestingly, COASTER is able to activate transcription in the presence of raloxifen, which compound is otherwise not an agonist in this system. This phenomenon is observed on ERα-mediated transcription, but not when ERβ is present as the estrogen receptor. Moreover, the coactivator GRIP1 is not able to activate expression of the reporter gene in the presence of raloxifen and ERα. The data show that the activity of the truncated form of COASTER, COASTERΔ, is identical to that of full length COASTER. This indicates that amino acids 1 to 234 are sufficient for the coactivating potential of COASTER on the raloxifen or 4OH-tamoxifen liganded ERα. The effects of COASTER on ERα mediated transcription were further studied by making dose-response curves for the ligands raloxifen and 4OH-tamoxifen in the presence and absence of COASTER. The data presented in FIG. 5 confirm the observation that raloxifen acts as an agonist on ERE-driven gene transcription in the presence of ERα and COASTER. When COASTER is omitted, raloxifen is not able to activate the reporter gene, even at high concentrations of the ligand. The anti-estrogen 4OH-tamoxifen is an agonist in this system. However, the expression of COASTER increases the magnitude of the transcriptional response. For both compounds, the activity of the reporter in the presence of ERα and COASTER is dependent on the concentration used in the assay.

The results presented here show that COASTER can influence the agonist/antagonist balance of mixed profile anti-estrogens such as raloxifen and 4OH-tamoxifen. Previous reports have shown that raloxifen may act as an agonist via non-classical (non-ERE) pathways on ERβ (Zou et al., Mol Endocrinol. 13, 418-430; Paech et al., Science 277, 1508-1510). To the best of our knowledge, these data provide the first observations of agonism of raloxifen on the classical estrogen-responsive element (ERE) pathway. In addition, these are the first indications that raloxifen may act as an agonist on ERα. These observations are important to our understanding of the mechanisms of action of anti-estrogens. The property of COASTER to activate the raloxifen-liganded ERα sets COASTER apart from the coactivators, such as GRIP1, described to date. Moreover, the assay described here can be used with particular adantage for the pharmacological screening of novel estrogen receptor ligands as COASTER is able to identify partial agonistic properties of compounds.

Tissue Distribution of COASTER

Figure 6:
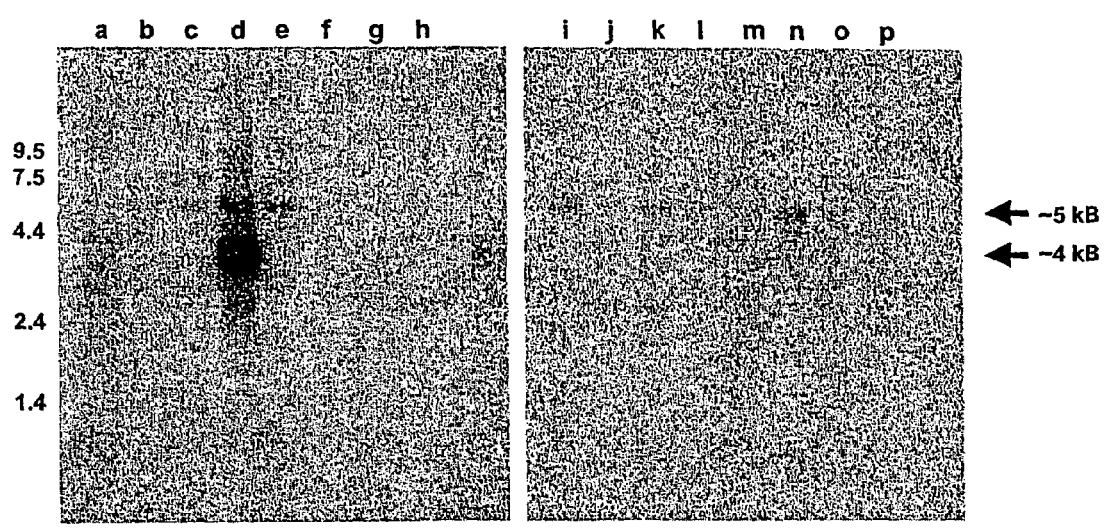
FIG. 6. Tissue distribution of COASTER transcripts. Human multiple tissue Northern blots were hybridised with a [$^{32}$P]-labeled COASTER cDNA probe. The figure shows an autoradiograph of the blots. The COASTER probe hybridises to two mRNA species of approximately 5 kB and 4 kB in size, indicated with arrows. The tissues represented on the blots include spleen (a), thymus (b), prostate (c), testis (d), ovary (e), small intestine (f), colon (g), peripheral blood leukocytes (h), heart (i), brain (j), placenta (k), lung (l), liver (m), skeletal muscle (n), kidney (o) and pancreas (p). The migration pattern of a size standard is indicated at the left side of the figure (size in kilobases).

The tissue distribution of COASTER mRNA was investigated by Northern blot analysis and RT-PCR. Human multiple tissue Northern blots were hybridized with a 794 bp COASTER cDNA fragment. Almost all tissues examined show hybridisation to an mRNA species of approximately 5 kB in size, with higher signals in testis, ovary, heart, placenta, and skeletal muscle, and lower to no signals in the other tissues (FIG. 6). In addition, a very strong hybridisation signal is observed to a 4 kB transcript that is uniquely present in testis. The size of the 5 kB transcript is in good agreement with the size of the cDNA that we have isolated. The 4 kB transcript may represent a splice-variant of which the detailed structure is as yet unknown. However, the testis specific expression pattern of this transcript is striking and suggests a functional role in testis physiology.

Figure 7:
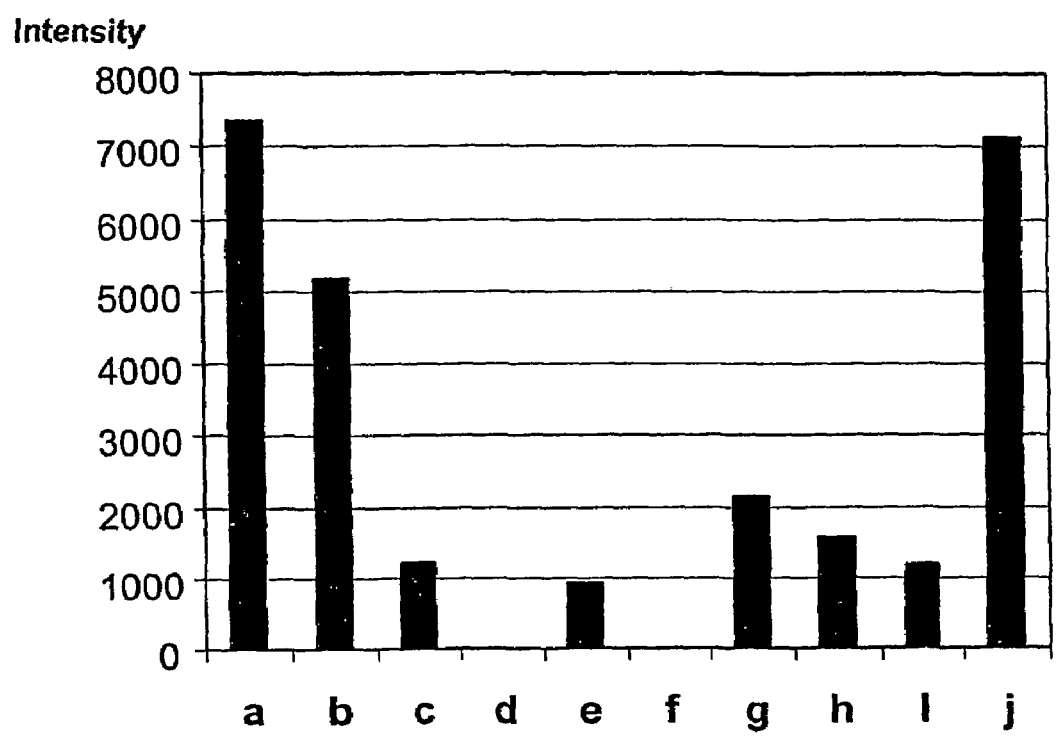
FIG. 7. COASTER expression in tumor cell lines. The relative expression levels of COASTER was determined by RT-PCR. The figure shows relative intensity of the PCR products as measured by scanning of the agarose gel electrophoresis images of the PCR products. The cell lines represented include: MCF-7 (a), T-47D (b), U-2 OS (c), MG63 (d), HOS (e), ECC-1 (f), Ishikawa (g), VE103 (h), HS760T (i) and SW 954 (j).
Figure 8:
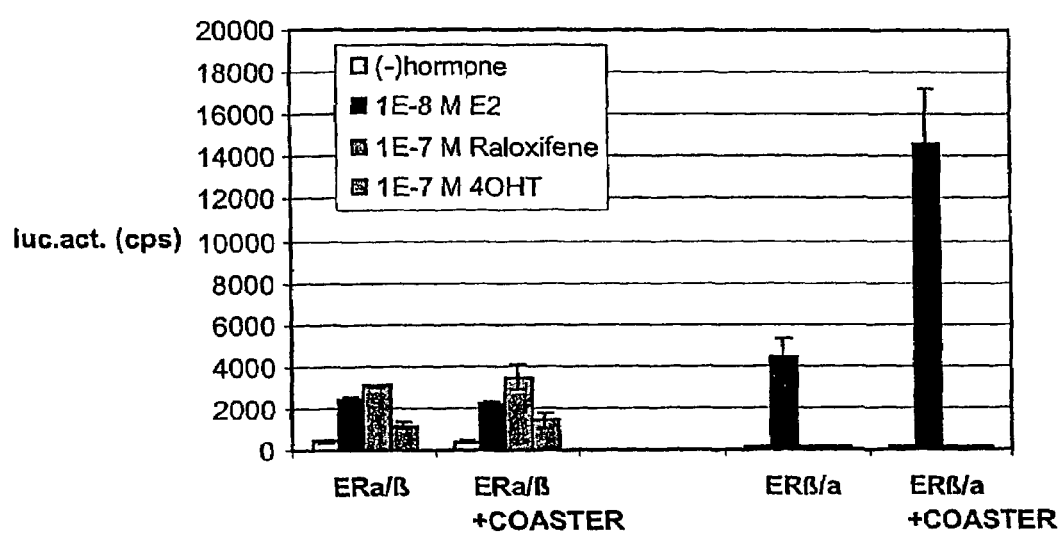
FIG. 8. Luciferase expression quatified with light counts per second (cps) in cells transfected with an ERβ/α chimeric receptor and COASTER in response to addition of estradiol (E2), raloxifene or 4-hydroxy-tamoxifen (4OHT).
Figure 9:
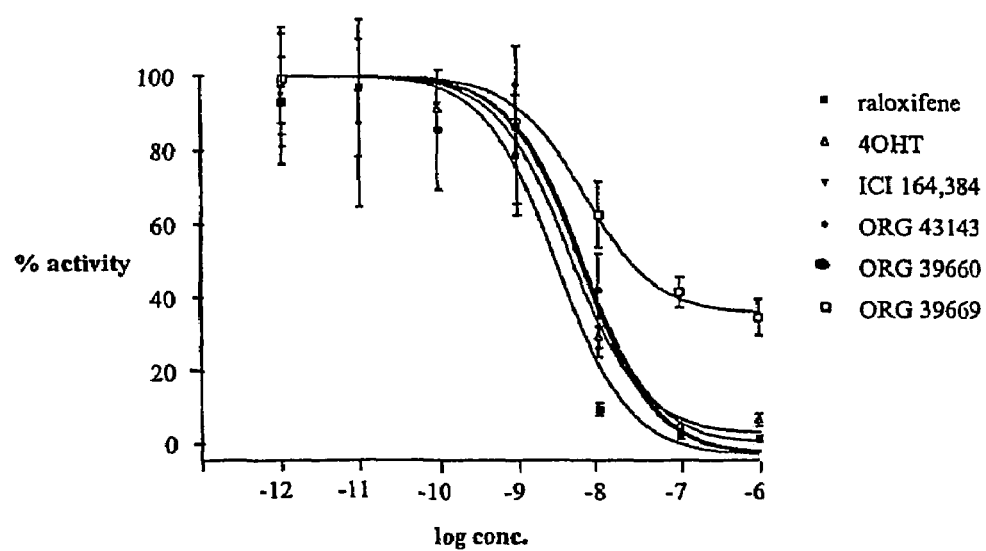
FIG. 9. Percentage estrogenic activity in response to addition of a standard dose of estradiol in the presence of various concentrations, expressed as logarithm of the concentration, of raloxifene, 4-hydroxy tamoxifen (4OHT), ICI 164,384, Org 43143, Org 39660 and Org 39669, respectively.
Figure 10:
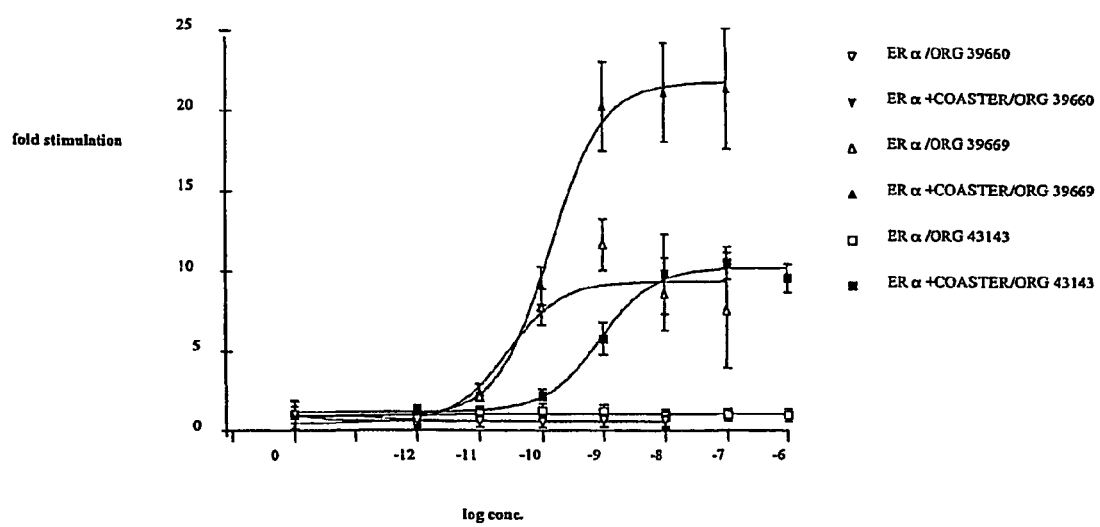
FIG. 10. Effect of compounds in a COASTER coactivation assay.
Figure 11:
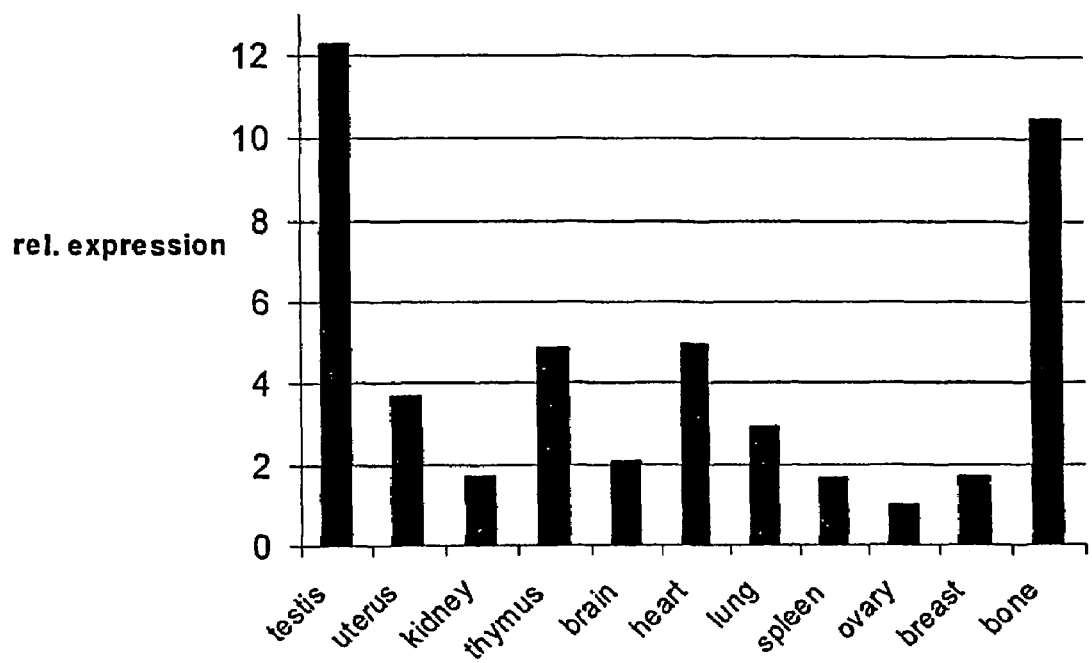
FIG. 11. COASTER expression in human and *M. fascicutlata* tissues. The relative expression levels of COASTER were determined by RT-PCR. The figure shows relative intensity of the PCR products as measured by a Taqman real-time quantitative PCR method. The tissues that served as the source for the RNA material are indicated at the bottom of the figure. All tissues were from human origin, except for the bone tissue which was derived from *M. fasciculata*.

Expression of mRNA from COASTER was also investigated by RT-PCR analysis in different human cell lines derived from tumors. The semi-quantitative results of the RT-PCR are shown in FIG. 7. The results show high expression in the breast epithelial carcinoma cell lines MCF-7 and T-47 and the vaginal epithelial cell line SW954. Moderate expression was observed in the osteosarcoma cell lines U-2 OS and HOS, the endometrial epithelial carcinoma cell line Ishikawa, the vascular endothelial cell line VE103ERα, and the endothelial cell line HS760T. No expression was detected in the osteosarcoma cell line MG63 and the endometrial epithelial carcinoma cell line ECC-1. The cell lines that show high expression of COASTER (MCF-7, T-47D, SW954) have been reported to contain high levels of ERα (Dechering et al., Curr. Med. Chem. 7, 561-576), indicating that COASTER can contribute to ERα-mediated growth of tumor cells.

Materials and Methods

Yeast Two Hybrid Screen

Yeast Media

Yeast host strains and transformants were cultured in complete medium (YPD) or in minimal Synthetic Dropout (SD) medium. The complete medium is a blend of peptone, yeast extract, and dextrose in optimal proportions for growth of yeast strains (see yeast protocols handbook Clontech, Palo Alta, USA, protocol PT3024-1). The minimal SD medium contains 2% dextrose, 0.67% yeast nitrogen base, and a specific mixture of amino acids and nucleosides (e.g. SD-His-Leu-Trp is a medium that lacks histidine, leucine and tryptophan). All these media were purchased from BIO101 (Beverly, USA).

Two-Hybrid Screen

*Saccharomyces cerevisiae* strain AH109 (MATa, trp1-901, leu2-3, 112, ura3-52, his3-200, gal4Δ, gal80Δ, LYS2::GAL1$_{UAS}$-GAL1$_{TATA}$-HIS3,GAL2$_{UAS}$-GAL2$_{TATA}$-ADE2, URA3::MEL1$_{TATA}$-lacZ) was obtained from Clontech, Palo Alto USA: To express the ERβ protein as a bait in yeast strain AH109, plasmid pGBT9.ERβ was used (kind gift of W. Kruijer, Rijksuniversiteit Groningen, The Netherlands). This plasmid contains the coding sequence of ERβ (amino acids 1 to 530) fused to a sequence encoding a GAL4 DNA binding domain and contains the TRP1 gene as a selectable marker. The yeast strain AH109 was transformed with pGBT9.ERβ, using a standard lithium-acetate method following the instruction manual from Clontech (Palo Alto, USA, protocol#PT3247-1) and transformants were selected on SD-Tryptophan (SD-Trp) plates.

From this plate single colonies were selected and stored as parental clones. Subsequently, the HIS3 background expression of these clones was determined by plating on the appropriate selection plates. Clones that grew on histidine-deficient media in the presence of 17β-estradiol were discarded. Subsequently, clones with low HIS3 background expression were transformed with a positive control pGRIP1 (kind gift of M. Stallcup, University of Southern California, USA), a plasmid that encodes the coactivator GRIP1 that has been shown to interact with the estrogen receptor in yeast (Hong et al., Mol. Cell. Biol. 17, 2735-2744). The parental clone (AH109.ERβ) that showed high HIS3 expression in the presence of pGRIP1 and 17β-estradiol was subsequently chosen as the recipient clone for screening of the library. A human osteosarcoma Matchmaker cDNA library was obtained from Clontech (Clontech, Palo Alto, USA, cat.#: HL4026AH). This library is constructed in vector pACT2, which contains a LEU2 gene as a selectable marker and expresses the cloned inserts in fusion with a GAL4-activation domain (AD). Recipient clone AH109.ERβ was transformed with 100 μg plasmid DNA from the osteosarcoma cDNA library. Transformants were selected on SD-Trp-Leu-His plates containing $10^{-8}$ M 17β-estradiol, and HIS$^+$ colonies were identified. HIS$^+$ colonies were rescreened by replica plating on SD-Trp-Leu-His-Ade media in the absence and presence of $10^{-8}$ M 17β-estradiol. Yeast transformants that showed a hormone dependent HIS$^+$/ADE$^+$ phenotype were selected for subsequent studies. From these transformants, DNA was isolated following a protocol for crude miniprep isolation (see basic protocols Y1.4). The crude miniprep was used to transform E. coli KC8 by electroporation and transformants containing the library-derived plasmid were selected on leucine deficient medium. Library inserts were sequenced on an ABI sequencer from Perkin Elmer (Norwalk, USA). Blast similarity searches were performed against the Incyte database.

Chemiluminescent Reporter Gene assay for β-galactosidase in yeast: A single colony was cultured in liquid SD-Trp-Leu medium overnight at 30° C. These overnight cultures were diluted to an $OD_{600}$ of 0.1 in 90 μl SD-Trp-Leu medium in a 96-well culture plate. 10 μl of a 10 times concentrated hormone stock solution were added and plates were incubated for 5 hours at 30° C. and under vigorous shaking at 200 rpm.

Subsequently, β-galactosidase activity was measured using the One-Step Yeast Lysis buffer and Galacton Plus chemiluminescent detection system of Tropix (Tropix, Inc., Avenue, Bedford, USA). Light emission was monitored using a Victor Instrument (Perkin Elmer, Norwalk, USA).

5' RACE (Rapid Amplification of cDNA Ends) of COASTER:

To isolate the 5' end of the COASTER cDNA, 5'RACE-PCR experiments were performed using Human testis Marathon-Ready cDNA (Clontech, Palo Alto, USA, Cat.# 7414-1). RACE PCR was performed using a Marathon cDNA amplification kit (Clontech, Palo Alto, USA) in combination with gene specific primer CCAGACACCCACGTGTGGCC following instructions of the manufacturer. Two distinct fragments (~650 bp and ~800 bp) were obtained. The fragments were isolated from an agarose gel, purified using Quaquick spin column (Qiagen, Valencia, USA) and cloned using the pCR2.1TOPO kit (Invitrogen, Carlsbad, USA). Colonies containing inserts were identified by colony PCR using gene specific primers CCAGACACCCACGTGTGGCC and AAGCCACCATGGACAGCAGGAGCAGTGGTG. Sequence analysis of positive clones was performed on an ABI sequencer (Perkin Elmer, Norwalk, USA).

Recombinant Plasmids:

Initially, a plasmid encoding a truncated form of COASTER (pACT2.COASTERΔ, amino acids 1-234) was isolated in the yeast two hybrid screen. The insert from this plasmid was cloned in the mammalian cell expression vector pCDNA3.1HISA (Invitrogen, Carlsbad, USA) to yield plasmid pCDNA3.1HISA.COASTERΔ. A plasmid containing the 3' end of the COASTER cDNA was obtained from Incyte Genomics (Palo Alto, USA). This plasmid (Incyte clone ID 2905757) was digested with SacI/NotI (amino acid 330 to 1061). The 5' end of the COASTER (amino acid 1 to 332) was amplified by PCR on human-testis Marathon Ready cDNA (Clontech, Palo Alto, USA, cat.#7414-1) using primers CTAGGTACCGGACAGCAGGAGCAGTGGTGC (SEQ ID 15) and GGCAGTGAGCTCCATGTGGG (SEQ ID 16) (restriction sites are underlined). The resulting PCR product was digested with KpnI and SacI and ligated together with the SacI-NotI restriction fragment into the KpnI-NotI restricted pCDNA3.1HISC vector (Invitrogen, Carlsbad, USA). The latter plasmid was termed pCDNA3.1HISC.COASTER. For transfection studies, the protein coding regions of the cDNA's for the human estrogen receptors α and β and the glucocorticoid receptor, were inserted into the mammalian expression vector pNGV1 (accession number X99274). The protein coding region of the progesterone receptor was inserted into the mammalian expression vector pKCRE (Stam et al., Eur. J. Pharmacol. 227,153). The reporter plasmid pMMTV-LUC was constructed by modification of vector pManMneoLUC (Clontech, Palo Alto, USA). The neomycin cassette was removed by digestion with endoR HindIII/BamHI, followed by blunting with Klenow polymerase, and ligation by T4 DNA ligase. The reporter vector 4ERE.TATALuc contains a luciferase gene under control of four estrogen-response elements (ERE) and was a gift from P. v.d. Saag (Nederlands Instituut voor Ontwikkelingsbiologie, Utrecht, The Netherlands). A mammalian expression plasmid for GRIP1 was constructed by restriction digestion of pGRIP1 (kind gift of M. Stallcup, University of Southern California, USA) with EcoRI and BamHI. The resulting fragment was ligated into a EcoRI/BamHI digested pCDNA3.1HISC vector to yield plasmid pCDNA3.1HISC.GRIP1.

Cell Culture and Transient Transfection:

U-2 OS cells were obtained from ATTC (HTB-96) and maintained at 37° C. in a humidified atmosphere (5% $CO_2$) as a monolayer culture in phenolred-free M505 medium. The latter medium consists of a mixture (1:1) of Dulbecco's Modified Eagle's Medium (DMEM, Gibco BRL,Breda, the Netherlands) and Nutrient Medium F12 (Ham's F12, Gibco BRL,Breda, the Netherlands) supplemented with 2.5 mg/ml sodium carbonate, 55 μg/ml sodium pyruvate, 2.3 μg/ml β-mercaptomethanol, 1.2 μg/ml ethanolamine, 360 μg/ml L-glutamine, 0.45 μg/ml sodium selenite, 62.5 μg/ml streptomycin, and 5% charcoal-treated bovine calf serum (Hyclone). $1.10^5$ cells were seeded in 24-wells tissue culture plates and DNA was introduced by use of lipofectin (Gibco BRL,Breda, the Netherlands). To this end, plasmid DNAs in 62.5 μl Optimem (Gibco BRL Breda, the Netherlands) was mixed with an equal volume of diluted lipofectin reagent (1.75 μl lipofectin in 62.5 μl Optimem) and allowed to stand at room temperature for 30 min. After washing the cells once with serum-free M505 medium, 250 μl Optimem together with the DNA-lipofectin mixture was added to the cells. After incubation for a 5 hour period at 37° C. (5% $CO_2$) cells were washed once with M505 medium supplemented with 5% charcoal-treated bovine calf serum and hormones were added to the medium. Cells were incubated overnight at 37° C. The next day, cells were washed once with phosphate buffered saline (PBS) and cell extracts were made by addition of 75 μl lysis buffer (0.1 M phosphate buffer pH 7.8, 0.2% Triton X-100). After incubation for 5 min at room temperature, a 30 μl aliquot was added to 50 μl luciferase assay reagent (Promega; Wisconsin, USA). Light emission was measured using a Victor Instrument (Perkin Elmer, Norwalk, USA).

Northern Blot Analysis:

Plasmid pCDNA3.1HISA.COASTERΔ was digested with EcoRI and XbaI to generate a probe (nucleotides 183-928). The DNA fragment was labeled with [$\alpha^{32}$P]dCTP with Ready-To Go DNA labeling beads following instructions of the manufacturer (Pharmacia). Human multiple tissue northern blots (Clontech, Palo Alto, USA, cat.# 7760-1 and 7759-1) were hybridized with the $\alpha^{32}$PdCTPlabelled DNA fragment (see basic protocols R1.5). Northern blots were washed using the following washing conditions: 2×30 min. 2×SSC/0.1% SDS at 65° C. and 1×15 min. 1×SSC/0.1% SDS at 65° C.

RT-PCR Analysis of COASTER Expression in Cell Lines:

cDNA was made using 2 μg of total RNA, isolated from a number of human cell lines using RNAzol B (Cinna/Biotecx), using the SuperscriptII kit (BRL). A portion of cDNA was used for specific PCR amplification of COASTER (primers sense TGAGGCATCTGAGTCAACA and anti sense CGAGCCAGAGTTAAAGCA. After 20, 25, 30 and 35 PCR-cycles, samples were taken. The PCR samples were analyzed on 1.5% agarose gels. Gel images were quantified with Imagequant 5.0 (Molecular dynamics).

In Vitro Translation:

A TnT Coupled Reticulocyte Lysate Systems (Promega, Madison, USA, cat.#L5020) was used for in vitro transcription/translation of COASTER from a pCDNA3.1HISC.COASTER template in the presence of [$^{35}$S]-methionine following instructions provided with the lysate. A fragment of SRC-1 encoded by plasmid pBK-SRC-1 (Onate et al., Science 270, 1354-1357) was analyzed in parallel as a control. Labeled proteins were separated by SDS-PAGE and visualized by autoradiography.

We claim:

1. An in vitro screening method for determining the transcription modulating activity of an agent, comprising:
providing a cell-based transcription system comprising a coactivator having at least 95% similarity with amino acids 1-234 of SEQ ID NO:7 or amino acids 1-234 of SEQ ID NO:8, a nuclear receptor responsive to the coactivator and a reporter gene whose transcription is promoted by the combination of the responsive nuclear receptor and the coactivator;
adding the agent to the cell-based transcription system;
quantifying the degree of transcription of the reporter gene in the presence of the agent; and
comparing the degree of transcription of the reporter gene in the presence of the agent with the degree of transcription of the reporter gene in the absence of the agent, thereby determining the transcription modulating activity of the agent.

2. The in vitro screening method of claim 1, wherein the coactivator has at least 95% similarity with amino acids 1-234 of SEQ ID) NO:7.

3. The in vitro screening method of claim 2, wherein the responsive nuclear receptor is a steroid receptor.

4. The in vitro screening method of claim 3, wherein the steroid receptor is selected from the group consisting of a progesterone receptor, an estrogen receptor and a glucocorticoid receptor.

5. The in vitro screening method of claim 2, wherein the coactivator has at least 95% similarity with SEQ ID NO:7.

6. The in vitro screening method of claim 5, wherein the responsive nuclear receptor is a steroid receptor.

7. The in vitro screening method of claim 6, wherein the steroid receptor is selected from the group consisting of a progesterone receptor, an estrogen receptor and a glucocorticoid receptor.

8. The in vitro screening method of claim 5, wherein the coactivator is SEQ ID NO:7.

9. The in vitro screening method of claim 8, wherein the responsive nuclear receptor is a steroid receptor.

10. The in vitro screening method of claim 9, wherein the steroid receptor is selected from the group consisting of a progesterone receptor, an estrogen receptor and a glucocorticoid receptor.

11. The in vitro screening method of claim 1, wherein the coactivator has at least 95% similarity with amino acids 1-234 of SEQ ID NO:8.

12. The in vitro screening method of claim 11, wherein the responsive nuclear receptor is a steroid receptor.

13. The in vitro screening method of claim 12, wherein the steroid receptor is selected from the group consisting of a progesterone receptor, an estrogen receptor and a glucocorticoid receptor.

14. The in vitro screening method of claim 11, wherein the coactivator has at least 95% similarity with SEQ ID NO:8.

15. The in vitro screening method of claim 14, wherein the responsive nuclear receptor is a steroid receptor.

16. The in vitro screening method of claim 15, wherein the steroid receptor is selected from the group consisting of a progesterone receptor, an estrogen receptor and a glucocorticoid receptor.

17. The in vitro screening method of claim 14, wherein the coactivator is SEQ ID NO:8.

18. The in vitro screening method of claim 17, wherein the responsive nuclear receptor is a steroid receptor.

19. The in vitro screening method of claim 18, wherein the steroid receptor is selected from the group consisting of a progesterone receptor, an estrogen receptor and a glucocorticoid receptor.

* * * * *

SEQUENCE LISTING

```
<160> NUMBER OF SEQ ID NOS: 16

<210> SEQ ID NO 1
<211> LENGTH: 4999
<212> TYPE: DNA
<213> ORGANISM: Homo sapiens

<400> SEQUENCE: 1
ggaagcccgg gagtgagaga aagcggctcc gggggcatag cgggccagta agggccgctc    60
ctcctttgaa gaggttttgc gtctctttcc gccggtggcg tcggcgctca cgcaggggcg   120
ggtcccggta gcgccaggcg gtgcagggcg ggaaggggat tcgtggcgac ggcggcggca   180
agggacagca ggagcagtgg tgctgtcagc gcggccgtcg gagacatggg agacccgggg   240
tcggagataa tagaatctgt ccctccagct ggccctgagg catctgagtc aacaacggat   300
gaaaatgaag acgacattca gtttgtcagt gaaggaccat tacgacctgt tcttgaatac   360
attgatctgg tcagcagtga tgatgaagag cctagcacct cttatactga tgagaatatt   420
aaacgtaaag accatattga ttatcagaag gataaagttg ctttaactct ggctcgtcta   480
gcccgccatg ttgaagtgga gaaacagcag aaagaagaga agaatagagc attcagaaga   540
aaaattgatt tcagcatgc tcatgggtta caagaattgg aatttattcg aggacattct   600
gatacagaag cagcaagact gtgtgtggac cagtggctaa aaatgccagg actcaaaaca   660
ggcacaatta attgtggaac aaaaagttca ttccgaagag gaggccacac gtgggtgtct   720
gggaaaccaa ttttatgtcc tataatgcac tgtaacaagg agtttgacaa tgggcacctt   780
ctcttaggac atttgaaaag gttcgatcac tctccatgtg atccaacaat tacactacat   840
ggacctttct tcagctcctt tgcttgtgta gtatgttata aaaaatttgt tactcaacaa   900
caatatagag atcacctttt tgataaggaa gccacagatg atggacataa caacaacctt   960
cttcctcaga ttattcagtg ttttgcatgt ccaaattgct tccttctttt tagcagaaag  1020
gaggagtgtt caaagcatat gtctggaaag aatcatttcc atcagagttt caaactgggt  1080
gataacaaag gaattgcaca tccaatatct ttcccatctt ttgcaaagaa acttttgatc  1140
tctctgtgca aagatgttcc ctttcaagtt aagtgtgtgg cctgccacaa gacactgcgt  1200
tcccacatgg agctcactgc ccatttcaga gttcattgtc gaaatgctgg acctgtagct  1260
gtagctgaga agagcattac ccaggttgca gagaaattca tattaagagg ttattgtcca  1320
gattgcaatc aagtctttgt ggatgaaacc agcacccaaa atcataagca gaattcagga  1380
cacaaagtcc gagtcattaa ctcagtggaa gaatcagtct tactctattg ccacagcagc  1440
gaagggaaca aggatccttc ttctgacttg catttattgt tggatcaatc aaaattttca  1500
```

-continued

```
tcacttaaaa gaaccatgtc tattaaagaa tctagctcac tggagtgcat tgccattcca    1560
aaaaagaaga tgaatttaaa agataaaagc catgaaggtg ttgcttgtgt ccagaaagaa    1620
aaatcagtag ttaaaacctg gttctgtgaa tgcaatcagc gattcccaag tgaagatgca    1680
gtagaaaagc atgttttctc agcaaacaca atgggttata aatgtgtggt ctgtggaaag    1740
gtatgtgatg attcagggt cattcgttta cacatgagcc ggattcacgg agggcacat     1800 ttaaataact ttcttttctg gtgtcggaca tgcaaaaagg agttaacaag gaaagatact    1860
atcatggcac atgtgactga atttcataat ggacacagat attttatga gatggatgag     1920 gtagaaggtg aaactttgcc atcatcctct acaacattgg ataatttgac tgctaacaag    1980
ccttcatcag ctattactgt tattgatcat tccccggcaa atagttctcc gagggtaaa     2040 tggcaatgcc ggatttgtga agatatgttt gattcccagg aatatgtaaa acagcactgc    2100
atgtctttgg caagccacaa gtttcataga tacagctgtg ctcactgcag aaagcctttt    2160
cataagatag aaacattgta ccgacattgc caagatgagc atgacaatga gataaagatt    2220
aaatacttct gtgggctttg tgatcttatc tttaatgtgg aagaagcatt tctgagtcat    2280
tatgaggagc accacagcat agattatgta tttgtgtcag aaaaaactga aacttcaatt    2340
aaaaccgaag atgattttcc agtaatagag accagtaacc agttaacttg tggttgccgt    2400
gagagttaca tctgtaaagt caacagaaaa gaagattata gcagatgtct ccaaatcatg    2460
ctggataaag gaaaactgtg gtttcgctgc agtttatgtt cggcaacagc acagaattta    2520
accgacatga acactcatat ccatcaagtg cacaaagaaa agagtgatga ggaggagcag    2580
cagtatgtaa tcaagtgtgg cacctgcacc aaagcatttc atgatcctga gagtgcacag    2640
cagcatttcc atagaaaaca ttgcttctta cagaaaccca gtgtggctca ttttggatct    2700
gaaaaatcaa acctgtacaa gtttactgct agtgcctcac atacagagag aaaactgaaa    2760
caggcaataa actattcaaa aagtttagac atggagaaag gagttgagaa tgacctaagc    2820
tatcagaata taggaggaaa caccaattgg aagcctccgc tcaactgtaa gatttataac    2880
tacctgaaca ggattggatg cttcttcctt catcctcgct gtagtaaaag aaaagatgct    2940
gctgattttg ccatatgtat gcatgctggc cgtctagatg aacaactacc caagcaaatt    3000
cctttcacca tcctctcagg agatcaaggt tttctggagc tagagaatca atttaagaag    3060
actcagaggc cagctcatat actaaaccct caccacttag agggagatat gatgtgtgcc    3120
ttgttaaata gcatatctga taccaccaaa gaatgtgaca gtgatgataa catgggtgcc    3180
aaaaatactt caataggaga agaatttata tccacagaag atgtggaatt agaagaagct    3240
attagaagaa gtcttgagga aatgtaatta aagatattac cacacaacat caagtggcct    3300
tgaagagact gagataacga attcttgagt ttgttttcta aaggagacca gaaatccact    3360
attacaaatg tatttgaaaa catgtttttg ctttcatatg ttcaaaattt gatctttgtt    3420
ttgtattttt gtgctaatgt gcaaacatgt acagaagaaa tagaatacat gttcatgcaa    3480
atataaatta tgtattctaa tataggtgta acagtttccc agttaacttt gaatttatat    3540
atttagattt aaaggattaa aaaaaaggaa agctcttgac agttgtttcc caaatagcat    3600
tagttcttta attttatttg tactgtacaa atgatgctag tttattttt tagcagtgaa    3660 aatgaatata aaaaggtga cataggtcaa gttttccata aattctactt ctcatgtggc    3720
actattatat aataccttg agatctttgt ttatgtttat tagaagaggg taatggaaac    3780
tgatcatgga aacattttaaa attttatcag caatgttctt tgtgggtgcc atgcatatgt    3840
aaattattgc tttaattaga gcagcacatt gctaaaataa aaaatacacc ttaatttta    3900
```

-continued

```
agaaataatt taaatgaaac aatttccatt cctttacct gcttagactt ttatgtgact      3960
tgtatggtct cctggttaaa gggaatggtg tcagaatatt tgcataaaat tatttttcat      4020
aacagtcctt ttttatatat tggtgtaaac ataatattct tcaagaaata atgttgaaag      4080
cctactcagg aataatcttc cttaactctt taaatttta tttcatgtga agtgttttca       4140
gtttagttat tcactgaatt gtcagtttcc ttcatttggt attacatatt taattcttaa      4200
atattgaggc cccattgtga gtaataaaaa atacgacata agtagaagac taagaagggc      4260
ttgtcatatt atctttgtgt atatgcttca tgttatttaa ccagaaatgt cttatctcta      4320
aaaattttta gtagtaatta tttaccaaac ttaaaaacat ttctataaat ataaagcttt      4380
tctttatatt taagacaaaa tataaaggct agaatttggt tccttctctg taacactaaa      4440
tattttagtg tgaaattgaa ttttttttatt actatagtct tttcaatcta taatttgtgt     4500
ttttaatttc ttgatatgtc acttctgttc ctccctgctt gcatttttta aaaactagac      4560
attgtggctt gagaatttat caatcatctt tccgaaatga ccacattgtg cttttagttt      4620
gtatgtttaa gtggtcaagc aaggctctag gaggtagtca ctgagctgga ccttaaacac      4680
atctgcagga gctcacaaaa tgggagcaaa agaggcattc cagaaagaag agtagttaag      4740
cagatgtggg ggcagggcaa gaggagacag caccttgttg ccagagattc tacacaaagg      4800
tgtgatggac actgatgctc tattaagaag cttttgtggt gtgtgtggta gagaataatt      4860
aaggcttctg ataagacagg aaagggatat ttcatcatga ctgttaagaa aaggtaactg      4920
ggttgtttaa tgttttaatt gataattgtc actgatcgta tttctacttg ttaaataatt      4980
aaaaatcatc ttaaaattc                                                   4999
```

<210> SEQ ID NO 2
<211> LENGTH: 4999
<212> TYPE: DNA
<213> ORGANISM: Homo sapiens

<400> SEQUENCE: 2

```
ggaagcccgg gagtgagaga aagcggctcc gggggcatag cgggccagta agggccgctc        60
ctcctttgaa gaggttttgc gtctctttcc gccggtggcg tcggcgctca cgcaggggcg       120
ggtcccggta gcgccaggcg gtgcaggcg ggaaggggat tcgtggcgac ggcggcggca       180
agggacagca ggagcagtgg tgctgtcagc gcggccgtcg gagacatggg agacccgggg       240
tcggagataa tagaatctgt ccctccagct ggccctgagg catctgagtc aacaacggat       300
gaaaatgaag acgacattca gtttgtcagt gaaggaccat tacgacctgt tcttgaatac       360
attgatctgg tcagcagtga tgatgaagag cctagcacct cttatactga tgagaatatt       420
aaacgtaaag accatattga ttatcagaag gataaagttg ctttaactct ggctcgtcta       480
gcccgccatg ttgaagtgga gaaacagcag aaagaagaga agaatagagc attcagagaa       540
aaaattgatt ttcagcatgc tcatgggtta caagaattgg aatttattcg aggacattct       600
gatacagaag cagcaagact gtgtgtggac cagtggctaa aaatgccagg actcaaaaca       660
ggcacaatta attgtggaac aaaaagttca ttccgaagag gaggccacac gtgggtgtct       720
gggaaaccaa ctttatgtcc tataatgcac tgtaacaagg agtttgacaa tgggcacctt       780
ctcttaggac atttgaaaag gttcgatcac tctccatgtg atccaacaat tacactacat       840
ggacctttct tcagctccct tgcttgtgta gtatgtttata aaaaatttgt tactcaacaa       900
caatatagag atcaccttttt tgataaggaa gccacagatg atggacataa caacaacctt       960
```

```
cttcctcaga ttattcagtg ttttgcatgt ccaaattgct tccttctttt tagcagaaag    1020
gaggagtgtt caaagcatat gtctggaaag aatcatttcc atcagagttt caaactgggt    1080
gataacaaag gaattgcaca tccaatatct ttcccatctt ttgcaaagaa acttttgatc    1140
tctctgtgca aagatgttcc cttttcaagtt aagtgtgtgg cctgccacaa gacactgcgt    1200
tcccacatgg agctcactgc ccatttcaga gttcattgtc gaaatgctgg acctgtagct    1260
gtagctgaga gagcattac ccaggttgca gagaaattca tattaagagg ttattgtcca    1320
gattgcaatc aagtctttgt ggatgaaacc agcacccaaa atcataagca gaattcagga    1380
cacaaagtcc gagtcattaa ctcagtggaa gaatcagtct tactctattg ccacagcagc    1440
gaagggaaca aggatccttc ttctgacttg catttattgt tggatcaatc aaaattttca    1500
tcacttaaaa gaaccatgtc tattaaagaa tctagctcac tggagtgcat tgccattcca    1560
aaaaagaaga tgaatttaaa agataaaagc catgaaggtg ttgcttgtgt ccagaaagaa    1620
aaatcagtag ttaaaacctg gttctgtgaa tgcaatcagc gattcccaag tgaagatgca    1680
gtagaaaagc atgttttctc agcaaacaca atgggttata aatgtgtggt ctgtggaaag    1740
gtatgtgatg attcagggt cattcgttta cacatgagcc ggattcacgg aggggcacat    1800
ttaaataact ttcttttctg gtgtcggaca tgcaaaaagg agttaacaag gaaagatact    1860
atcatggcac atgtgactga atttcataat ggacacagat attttttatga gatggatgag    1920
gtagaaggtg aaactttgcc atcatcctct acaacattgg ataatttgac tgctaacaag    1980
ccttcatcag ctattactgt tattgatcat tccccggcaa atagttctcc gagggggtaaa    2040
tggcaatgcc ggatttgtga agatatgttt gattcccagg aatatgtaaa acagcactgc    2100
atgtctttgg caagccacaa gtttcataga tacagctgtg ctcactgcag aaagcctttt    2160
cataagatag aaacattgta ccgacattgc caagatgagc atgacaatga gataaagatt    2220
aaatacttct gtgggctttg tgatcttatc tttaatgtgg aagaagcatt tctgagtcat    2280
tatgaggagc accacagcat agattatgta tttgtgtcag aaaaaactga aacttcaatt    2340
aaaaccgaag atgattttcc agtaatagag accagtaacc agttaacttg tggttgccgt    2400
gagagttaca tctgtaaagt caacagaaaa gaagattata gcagatgtct ccaaatcatg    2460
ctggataaag gaaaactgtg gtttcgctgc agtttatgtt cggcaacagc acagaattta    2520
accgacatga acactcatat ccatcaagtg cacaaagaaa agagtgatga ggaggagcag    2580
cagtatgtaa tcaagtgtgg cacctgcacc aaagcatttc atgatcctga gagtgcacag    2640
cagcatttcc atagaaaaca ttgcttctta cagaaaccca gtgtggctca ttttggatct    2700
gaaaaatcaa acctgtacaa gtttactgct agtgcctcac atacagagag aaaactgaaa    2760
caggcaataa actattcaaa aagtttagac atggagaaag gagttgagaa tgacctaagc    2820
tatcagaata taggaggaaa caccaattgg aagcctccgc tcaactgtaa gatttataac    2880
tacctgaaca ggattggatg cttcttcctt catcctcgct gtagtaaaag aaaagatgct    2940
gctgattttg ccatatgtat gcatgctggc cgtctagatg aacaactacc caagcaaatt    3000
cctttcacca tcctctcagg agatcaaggt tttctggagc tagagaatca atttaagaag    3060
actcagaggc cagctcatat actaaaccct caccacttag agggagatat gatgtgtgcc    3120
ttgttaaata gcatatctga taccaccaaa gaatgtgaca gtgatgataa catgggtgcc    3180
aaaaatactt caataggaga agaatttata tccacagaag atgtggaatt agaagaagct    3240
attgaagaa gtcttgagga aatgtaatta aagatattac cacacaacat caagtggcct    3300
tgaagagact gagataacga attcttgagt ttgttttcta aaggagacca gaaatccact    3360
```

| | |
|---|---|
| attacaaatg tatttgaaaa catgttttg ctttcatatg ttcaaaattt gatctttgtt | 3420 |
| ttgtatttt gtgctaatgt gcaaacatgt acagaagaaa tagaatacat gttcatgcaa | 3480 |
| atataaatta tgtattctaa ataggtgta acagtttccc agttaacttt gaatttatat | 3540 |
| atttagattt aaaggattaa aaaaaggaa agctcttgac agttgtttcc caaatagcat | 3600 |
| tagttcttta attttatttg tactgtacaa atgatgctag tttatttttt tagcagtgaa | 3660 |
| aatgaatata aaaaaggtga cataggtcaa gttttccata aattctactt ctcatgtggc | 3720 |
| actattatat aataccttg agatctttgt ttatgtttat tagaagaggg taatggaaac | 3780 |
| tgatcatgga aacatttaaa attttatcag caatgttctt tgtgggtgcc atgcatatgt | 3840 |
| aaattattgc tttaattaga gcagcacatt gctaaaataa aaatacacc ttaattttta | 3900 |
| agaaataatt taaatgaaac aatttccatt cctttacct gcttagactt ttatgtgact | 3960 |
| tgtatggtct cctggttaaa gggaatggtg tcagaatatt tgcataaaat tatttttcat | 4020 |
| aacagtcctt ttttatatat tggtgtaaac ataatattct tcaagaaata atgttgaaag | 4080 |
| cctactcagg aataatcttc cttaactctt taaattttta tttcatgtga agtgttttca | 4140 |
| gtttagttat tcactgaatt gtcagtttcc ttcatttggt attacatatt taattcttaa | 4200 |
| atattgaggc cccattgtga gtaataaaaa atacgacata agtagaagac taagaagggc | 4260 |
| ttgtcatatt atctttgtgt atatgcttca tgttatttaa ccagaaatgt cttatctcta | 4320 |
| aaaattttta gtagtaatta tttaccaaac ttaaaaacat ttctataaat ataaagcttt | 4380 |
| tctttatatt taagacaaaa tataaaggct agaatttggt tccttctctg taacactaaa | 4440 |
| tattttagtg tgaaattgaa ttttttatt actatagtct tttcaatcta taatttgtgt | 4500 |
| ttttaatttc ttgatatgtc acttctgttc ctccctgctt gcatttttta aaaactagac | 4560 |
| attgtggctt gagaatttat caatcatctt tccgaaatga ccacattgtg cttttagttt | 4620 |
| gtatgtttaa gtggtcaagc aaggctctag gaggtagtca ctgagctgga ccttaaacac | 4680 |
| atctgcagga gctcacaaaa tgggagcaaa agaggcattc cagaaagaag agtagttaag | 4740 |
| cagatgtggg ggcagggcaa gaggagacag caccttgttg ccagagattc tacacaaagg | 4800 |
| tgtgatggac actgatgctc tattaagaag cttttgtggt gtgtgtggta gagaataatt | 4860 |
| aaggcttctg ataagacagg aaagggatat ttcatcatga ctgttaagaa aaggtaactg | 4920 |
| ggttgtttaa tgttttaatt gataattgtc actgatcgta tttctacttg ttaaataatt | 4980 |
| aaaaatcatc ttaaaattc | 4999 |

<210> SEQ ID NO 3
<211> LENGTH: 5144
<212> TYPE: DNA
<213> ORGANISM: Homo sapiens

<400> SEQUENCE: 3

| | |
|---|---|
| ggaagcccgg gagtgagaga aagcggctcc ggggggcatag cgggccagta agggccgctc | 60 |
| ctcctttgaa gaggttttgc gtctctttcc gccggtggcg tcggcgctca cgcaggggcg | 120 |
| ggtcccggta gcgccaggcg gtgcagggcg ggaagggat tcgtggcgac ggcggcggca | 180 |
| agggacagca ggagcagtgg tgctgtcagc gcggccgtcg gagacatggg agacccgggg | 240 |
| tcggagataa tagaatctgt ccctccagct ggccctgagg catctgagtc aacaacggat | 300 |
| gaaaatgaag acgacattca gtttgtcagt gaaggaccat tacgacctgt tcttgaatac | 360 |
| attgatctgg tcagcagtga tgatgaagag cctagcacct cttatactga tgagaatatt | 420 |

```
aaacgtaaag accatattga ttatcagaag gataaagttg ctttaactct ggctcgtcta    480
gcccgccatg ttgaagtgga gaaacagcag aaagaagaga agaatagagc attcagagaa    540
aaaattgatt ttcagcatgc tcatgggtta caagaattgg aatttattcg aggacattct    600
gatacagaag cagcaagact gtgtgtggac cagtggctaa aaatgccagg actcaaaaca    660
ggcacaatta attgtggaac aaaaagttca ttccgaagag gaggccacac gtgggtgtct    720
gggaaaccaa ttttatgtcc tataatgcac tgtaacaagg agtttgacaa tgggcaccttt    780 ctcttaggac atttgaaaag gttcgatcac tctccatgtg atccaacaat tacactacat    840
ggacctttct tcagctcctt tgcttgtgta gtatgttata aaaaatttgt tactcaacaa    900
caatatagag atcaccttt tgataaggaa gccacagatg atggacataa caacaacctt    960
cttcctcaga ttattcagtg ttttgcatgt ccaaattgct tccttctttt tagcagaaag   1020
gaggagtgtt caaagcatat gtctggaaag aatcatttcc atcagagttt caaactgggt   1080
gataacaaag gaattgcaca tccaatatct ttcccatctt ttgcaaagaa acttttgatc   1140
tctctgtgca aagatgttcc ctttcaagtt aagtgtgtgg cctgccacaa gacactgcgt   1200
tcccacatgg agctcactgc ccatttcaga gttcattgtc gaaatgctgg acctgtagct   1260
gtagctgaga agagcattac ccaggttgca gagaaattca tattaagagg ttattgtcca   1320
gattgcaatc aagtctttgt ggatgaaacc agcaccccaaa atcataagca gaattccagga   1380 cacaaagtcc gagtcattaa ctcagtggaa gaatcagtct tactctattg ccacagcagc   1440
gaagggaaca aggatccttc ttctgacttg catttattgt tggatcaatc aaaattttca   1500
tcacttaaaa gaaccatgtc tattaaagaa tctagctcac tggagtgcat tgccattcca   1560
aaaaagaaga tgaatttaaa agataaaagc catgaaggtg ttgcttgtgt ccagaaagaa   1620
aaatcagtag ttaaaacctg gttctgtgaa tgcaatcagc gattcccaag tgaagatgca   1680
gtagaaaagc atgttttctc agcaaacaca atgggttata atgtgtggt ctgtggaaag   1740 gtatgtgatg attcagggt cattcgttta cacatgagcc ggattcacgg aggggcacat   1800
ttaaataact ttctttttctg gtgtcggaca tgcaaaaagg agttaacaag gaaagatact   1860
atcatggcac atgtgactga atttcataat ggacacagat ttttttatga gatggatgag   1920
gtagaaggtg aaactttgcc atcatcctct acaacattgg ataatttgac tgctaacaag   1980
ccttcatcag ctattactgt tatttgatcat tccccggcaa atagttctcc gaggggtaaa   2040
tggcaatgcc ggatttgtga agatatgttt gattcccagg aatatgtaaa acagcactgc   2100
atgtctttgg caagccacaa gtttcataga tacagctgtg ctcactgcag aaagcctttt   2160
cataagatag aaacattgta ccgacattgc caagatgagc atgacaatga gataaagatt   2220
aaatacttct gtgggctttg tgatcttatc tttaatgtgg aagaagcatt tctgagtcat   2280
tatgaggagc accacagcat agattatgta tttgtgtcag aaaaaactga aacttcaatt   2340
aaaaccgaag atgattttcc agtaatagag accagtaacc agttaacttg tggttgccgt   2400
gagagttaca tctgtaaagt caacagaaaa gaagattata gcagatgtct ccaaatcatg   2460
ctggataaag gaaaactgtg gtttcgctgc agtttatgtt cggcaacagc acagaattta   2520
accgacatga acactcatat ccatcaagtg cacaaagaaa agagtgatga ggaggagcag   2580
cagtatgtaa tcaagtgtgg cacctgcacc aaagcatttc atgatcctga gagtgcacag   2640
cagcatttcc atagaaaaca ttgcttctta cagaaaccca gtgtggctca ttttggatct   2700
gaaaaatcaa acctgtacaa gtttactgct agtgcctcac atacagagag aaaactgaaa   2760
caggcaataa actattcaaa aagtttagac atggagaaag gagttgagaa tgacctaagc   2820
```

```
tatcagaata tagaggaaga aattgttgag cttccagatt tggattacct gcgaaccatg    2880
actcatatag tctttgtaga ttttgataac tggtcaaact ttttggtca tctaccaggg     2940 catctaaacc aaggaacatt tatttggggc tttcaaagga ggaaacacca attggaagcc    3000
tccgctcaac tgtaagattt ataactacct gaacaggatt ggatgcttct tccttcatcc    3060
tcgctgtagt aaaagaaaag atgctgctga ttttgccata tgtatgcatg ctggccgtct    3120
agatgaacaa ctacccaagc aaattccttt caccatcctc tcaggagatc aaggttttct    3180
ggagctagag aatcaattta agaagactca gaggccagct catatactaa accctcacca    3240
cttagaggga gatatgatgt gtgccttgtt aaatagcata tctgatacca ccaaagaatg    3300
tgacagtgat gataacatgg gtgccaaaaa tacttcaata ggagaagaat ttatatccac    3360
agaagatgtg gaattagaag aagctattag aagaagtctt gaggaaatgt aattaaagat    3420
attaccacac aacatcaagt ggccttgaag agactgagat aacgaattct tgagtttgtt    3480
ttctaaagga gaccagaaat ccactattac aaatgtattt gaaaacatgt ttttgctttc    3540
atatgttcaa aatttgatct ttgttttgta tttttgtgct aatgtgcaaa catgtacaga    3600
agaaatagaa tacatgttca tgcaaatata aattatgtat tctaatatag gtgtaacagt    3660
ttcccagtta actttgaatt tatatattta gatttaaagg attaaaaaaa aggaaagctc    3720
ttgacagttg tttcccaaat agcattagtt ctttaatttt atttgtactg tacaaatgat    3780
gctagtttat tttttagca gtgaaaatga atataaaaaa ggtgacatag gtcaagtttt     3840
ccataaattc tacttctcat gtggcactat tatataatac ctttgagatc tttgtttatg    3900
tttattagaa gagggtaatg gaaactgatc atggaaacat ttaaaatttt atcagcaatg    3960
ttctttgtgg gtgccatgca tatgtaaatt attgctttaa ttagagcagc acattgctaa    4020
aataaaaaat caccttaat ttttaagaaa taatttaaat gaaacaattt ccattccttt     4080
tacctgctta gactttatg tgacttgtat ggtctcctgg ttaaagggaa tggtgtcaga     4140
atatttgcat aaaattattt ttcataacag tcctttttta tatattggtg taaacataat    4200
attcttcaag aaataatgtt gaaagcctac tcaggaataa tcttccttaa ctcttttaat    4260
ttttatttca tgtgaagtgt tttcagttta gttattcact gaattgtcag tttccttcat    4320
ttggtattac atatttaatt cttaaatatt gaggccccat tgtgagtaat aaaaaatacg    4380
acataagtag aagactaaga agggcttgtc atattatctt tgtgtatatg cttcatgtta    4440
tttaaccaga aatgtcttat ctctaaaaat ttttagtagt aattatttac caaacttaaa    4500
aacatttcta taaatataaa gcttttcttt atatttaaga caaatataaa aggctagaat    4560
ttggttcctt ctctgtaaca ctaaatattt tagtgtgaaa ttgaattttt ttattactat    4620
agtcttttca atctataatt tgtgttttta atttcttgat atgtcacttc tgttcctccc    4680
tgcttgcatt ttttaaaaac tagacattgt ggcttgagaa tttatcaatc atctttccga    4740
aatgaccaca ttgtgctttt agtttgtatg tttaagtggt caagcaaggc tctaggaggt    4800
agtcactgag ctggacctta aacacatctg caggagctca caaatggga gcaaaagagg     4860 cattccagaa agaagagtag ttaagcagat gtgggggcag ggcaagagga gacagcacct    4920
tgttgccaga gattctacac aaaggtgtga tggacactga tgctctatta agaagctttt    4980
gtggtgtgtg tggtagagaa taattaaggc ttctgataag acaggaaagg gatatttcat    5040
catgactgtt aagaaaaggt aactgggttg tttaatgttt taattgataa ttgtcactga    5100
tcgtatttct acttgttaaa aattaaaaaa tcatcttaaa attc                     5144
```

<210> SEQ ID NO 4
<211> LENGTH: 5144
<212> TYPE: DNA
<213> ORGANISM: Homo sapiens

<400> SEQUENCE: 4

| | | | | | | |
|---|---|---|---|---|---|---|
| ggaagcccgg | gagtgagaga | aagcggctcc | gggggcatag | cgggccagta | agggccgctc | 60 |
| ctcctttgaa | gaggttttgc | gtctctttcc | gccggtggcg | tcggcgctca | cgcaggggcg | 120 |
| ggtcccggta | gcgccaggcg | gtgcagggcg | ggaaggggat | tcgtggcgac | ggcggcggca | 180 |
| agggacagca | ggagcagtgg | tgctgtcagc | gcggccgtcg | gagacatggg | agacccgggg | 240 |
| tcggagataa | tagaatctgt | ccctccagct | ggccctgagg | catctgagtc | aacaacggat | 300 |
| gaaaatgaag | acgacattca | gtttgtcagt | gaaggaccat | tacgacctgt | tcttgaatac | 360 |
| attgatctgg | tcagcagtga | tgatgaagag | cctagcacct | cttatactga | tgagaatatt | 420 |
| aaacgtaaag | accatattga | ttatcagaag | gataaagttg | ctttaactct | ggctcgtcta | 480 |
| gcccgccatg | ttgaagtgga | gaaacagcag | aaagaagaga | gaatagagc | attcagagaa | 540 |
| aaaattgatt | ttcagcatgc | tcatgggtta | caagaattgg | aatttattcg | aggacattct | 600 |
| gatacagaag | cagcaagact | gtgtgtggac | cagtggctaa | aaatgccagg | actcaaaaca | 660 |
| ggcacaatta | ttgtggaac | aaaaagttca | ttccgaagag | gaggccacac | gtgggtgtct | 720 |
| gggaaaccaa | ctttatgtcc | tataatgcac | tgtaacaagg | agtttgacaa | tgggcacctt | 780 |
| ctcttaggac | atttgaaaag | gttcgatcac | tctccatgtg | atccaacaat | tacactacat | 840 |
| ggacctttct | tcagctcctt | tgcttgtgta | gtatgttata | aaaaatttgt | tactcaacaa | 900 |
| caatatagag | atcacctttt | tgataaggaa | gccacagatg | atggacataa | caacaacctt | 960 |
| cttcctcaga | ttattcagtg | ttttgcatgt | ccaaattgct | tccttctttt | tagcagaaag | 1020 |
| gaggagtgtt | caaagcatat | gtctggaaag | aatcatttcc | atcagagttt | caaactgggt | 1080 |
| gataacaaag | gaattgcaca | tccaatatct | ttcccatctt | ttgcaaagaa | acttttgatc | 1140 |
| tctctgtgca | aagatgttcc | ctttcaagtt | aagtgtgtgg | cctgccacaa | gacactgcgt | 1200 |
| tcccacatgg | agctcactgc | ccatttcaga | gttcattgtc | gaaatgctgg | acctgtagct | 1260 |
| gtagctgaga | gagcattac | ccaggttgca | gagaaattca | tattaagagg | ttattgtcca | 1320 |
| gattgcaatc | aagtctttgt | ggatgaaacc | agcacccaaa | atcataagca | gaattcagga | 1380 |
| cacaaagtcc | gagtcattaa | ctcagtggaa | gaatcagtct | tactctattg | ccacagcagc | 1440 |
| gaagggaaca | aggatccttc | ttctgacttg | catttattgt | tggatcaatc | aaaattttca | 1500 |
| tcacttaaaa | gaaccatgtc | tattaaagaa | tctagctcac | tggagtgcat | tgccattcca | 1560 |
| aaaaagaaga | tgaatttaaa | agataaaagc | catgaaggtg | ttgcttgtgt | ccagaaagaa | 1620 |
| aaatcagtag | ttaaaacctg | gttctgtgaa | tgcaatcagc | gattcccaag | tgaagatgca | 1680 |
| gtagaaaagc | atgttttctc | agcaaacaca | atgggttata | atgtgtggt | ctgtggaaag | 1740 |
| gtatgtgatg | attcaggggt | cattcgttta | cacatgagcc | ggattcacgg | aggggcacat | 1800 |
| ttaaataact | ttcttttctg | gtgtcggaca | tgcaaaaagg | agttaacaag | gaaagatact | 1860 |
| atcatggcac | atgtgactga | atttcataat | ggacacagat | atttttatga | gatggatgag | 1920 |
| gtagaaggtg | aaactttgcc | atcatcctct | acaacattgg | ataatttgac | tgctaacaag | 1980 |
| ccttcatcag | ctattactgt | tattgatcat | tccccggcaa | atagttctcc | gagggggtaaa | 2040 |
| tggcaatgcc | ggatttgtga | agatatgttt | gattcccagg | aatatgtaaa | acagcactgc | 2100 |
| atgtctttgg | caagccacaa | gtttcataga | tacagctgtg | ctcactgcag | aaagcctttt | 2160 |

```
cataagatag aaacattgta ccgacattgc caagatgagc atgacaatga gataaagatt    2220
aaatacttct gtgggctttg tgatcttatc tttaatgtgg aagaagcatt tctgagtcat    2280
tatgaggagc accacagcat agattatgta tttgtgtcag aaaaaactga aacttcaatt    2340
aaaaccgaag atgattttcc agtaatagag accagtaacc agttaacttg tggttgccgt    2400
gagagttaca tctgtaaagt caacagaaaa gaagattata gcagatgtct ccaaatcatg    2460
ctggataaag gaaaactgtg gtttcgctgc agtttatgtt cggcaacagc acagaattta    2520
accgacatga acactcatat ccatcaagtg cacaaagaaa agagtgatga ggaggagcag    2580
cagtatgtaa tcaagtgtgg cacctgcacc aaagcatttc atgatcctga gagtgcacag    2640
cagcatttcc atagaaaaca ttgcttctta cagaaaccca gtgtggctca ttttggatct    2700
gaaaaatcaa acctgtacaa gtttactgct agtgcctcac atacagagag aaaactgaaa    2760
caggcaataa actattcaaa aagtttagac atggagaaag gagttgagaa tgacctaagc    2820
tatcagaata tagaggaaga aattgttgag cttccagatt tggattacct gcgaaccatg    2880
actcatatag tctttgtaga ttttgataac tggtcaaact ttttggtca tctaccaggg     2940 catctaaacc aaggaacatt tatttggggc tttcaaagga ggaaacacca attggaagcc    3000
tccgctcaac tgtaagattt ataactacct gaacaggatt ggatgcttct tccttcatcc    3060
tcgctgtagt aaaagaaaag atgctgctga ttttgccata tgtatgcatg ctggccgtct    3120
agatgaacaa ctacccaagc aaattccttt caccatcctc tcaggagatc aaggttttct    3180
ggagctagag aatcaattta agaagactca gaggccagct catatactaa accctcacca    3240
cttagaggga gatatgatgt gtgccttgtt aaatagcata tctgatacca ccaaagaatg    3300
tgacagtgat gataacatgg gtgccaaaaa tacttcaata ggagaagaat ttatatccac    3360
agaagatgtg gaattagaag aagctattag aagaagtctt gaggaaatgt aattaaagat    3420
attaccacac aacatcaagt ggccttgaag agactgagat aacgaattct tgagtttgtt    3480
ttctaaagga gaccagaaat ccactattac aaatgtattt gaaaacatgt ttttgctttc    3540
atatgttcaa aatttgatct ttgttttgta tttttgtgct aatgtgcaaa catgtacaga    3600
agaaatagaa tacatgttca tgcaaatata aattatgtat tctaatatag gtgtaacagt    3660
ttcccagtta actttgaatt tatatattta gatttaaagg attaaaaaaa aggaaagctc    3720
ttgacagttg tttcccaaat agcattagtt ctttaatttt atttgtactg tacaaatgat    3780
gctagtttat ttttttagca gtgaaaatga atataaaaaa ggtgacatag gtcaagtttt    3840
ccataaattc tacttctcat gtggcactat tatataatac ctttgagatc tttgtttatg    3900
tttattagaa gagggtaatg gaaactgatc atggaaacat ttaaaatttt atcagcaatg    3960
ttctttgtgg gtgccatgca tatgtaaatt attgctttaa ttagagcagc acattgctaa    4020
aataaaaaat acaccttaat ttttaagaaa taatttaaat gaaacaattt ccattccttt    4080
tacctgctta gacttttatg tgacttgtat ggtctcctgg ttaaagggaa tggtgtcaga    4140
atatttgcat aaaattattt ttcataacag tcctttttta tatattggtg taaacataat    4200
attcttcaag aaataatgtt gaaagcctac tcaggaataa tcttccttaa ctctttaaat    4260
ttttatttca tgtgaagtgt tttcagttta gttattcact gaattgtcag tttccttcat    4320
ttggtattac atatttaatt cttaaatatt gaggcccccat tgtgagtaat aaaaaatacg    4380
acataagtag aagactaaga agggcttgtc atattatctt tgtgtatatg cttcatgtta    4440
tttaaccaga aatgtcttat ctctaaaaat ttttagtagt aattatttac caaacttaaa    4500
```

-continued

```
aacatttcta taaatataaa gcttttcttt atatttaaga caaaatataa aggctagaat    4560
ttggttcctt ctctgtaaca ctaaatattt tagtgtgaaa ttgaattttt ttattactat    4620
agtcttttca atctataatt tgtgttttta atttcttgat atgtcacttc tgttcctccc    4680
tgcttgcatt ttttaaaaac tagacattgt ggcttgagaa tttatcaatc atctttccga    4740
aatgaccaca ttgtgctttt agtttgtatg tttaagtggt caagcaaggc tctaggaggt    4800
agtcactgag ctggacctta acacatctg caggagctca caaaatggga gcaaagagg     4860 cattccagaa agaagagtag ttaagcagat gtggggcag gcaagagga gacagcacct     4920 tgttgccaga gattctacac aaaggtgtga tggacactga tgctctatta agaagctttt    4980
gtggtgtgtg tggtagagaa taattaaggc ttctgataag acaggaaagg gatatttcat    5040
catgactgtt aagaaaaggt aactgggttg tttaatgttt taattgataa ttgtcactga    5100
tcgtatttct acttgttaaa taattaaaaa tcatcttaaa attc                    5144
```

<210> SEQ ID NO 5
<211> LENGTH: 3042
<212> TYPE: DNA
<213> ORGANISM: Homo sapiens

<400> SEQUENCE: 5

```
atgggagacc cggggtcgga gataatagaa tctgtccctc cagctggccc tgaggcatct      60
gagtcaacaa cggatgaaaa tgaagacgac attcagtttg tcagtgaagg accattacga    120
cctgttcttg aatacattga tctggtcagc agtgatgatg aagagcctag cacctcttat    180
actgatgaga atattaaacg taaagaccat attgattatc agaaggataa agttgcttta    240
actctggctc gtctagcccg ccatgttgaa gtggagaaac agcagaaaga agagaagaat    300
agagcattca gagaaaaaat tgattttcag catgctcatg ggttacaaga attggaattt    360
attcgaggac attctgatac agaagcagca agactgtgtg tggaccagtg gctaaaaatg    420
ccaggactca aaacaggcac aattaattgt ggaacaaaaa gttcattccg aagaggaggc    480
cacacgtggg tgtctgggaa accaattta tgtcctataa tgcactgtaa caaggagttt    540
gacaatgggc accttctctt aggacatttg aaaaggttcg atcactctcc atgtgatcca    600
acaattacac tacatggacc tttcttcagc tcctttgctt gtgtagtatg ttataaaaaa    660
tttgttactc aacaacaata tagagatcac cttttttgata aggaagccac agatgatgga    720
cataacaaca accttcttcc tcagattatt cagtgttttg catgtccaaa ttgcttcctt    780 cttttttagca gaaaggagga gtgttcaaag catatgtctg gaaagaatca tttccatcag    840
agtttcaaac tgggtgataa caaaggaatt gcacatccaa tatctttccc atcttttgca    900
aagaaacttt tgatctctct gtgcaaagat gttcccttc aagttaagtg tgtggcctgc    960
cacaagacac tgcgttccca catggagctc actgcccatt tcagagttca ttgtcgaaat   1020
gctgaacctg tagctgtagc tgagaagagc attacccagg ttgcagagaa attcatatta   1080
agaggttatt gtccagattg caatcaagtc tttgtggatg aaaccagcac ccaaaatcat   1140
aagcagaatt caggacacaa agtccgagtc attaactcag tggaagaatc agtcttactc   1200
tattgccaca gcagcgaagg gaacaaggat ccttcttctg acttgcattt attgttggat   1260
caatcaaaat tttcatcact aaaagaacc atgtctatta agaatctag ctcactggag    1320 tgcattgcca ttccaaaaaa gaagatgaat ttaaaagata aagccatga aggtgttgct    1380 tgtgtccaga agaaaaaatc agtagttaaa acctggttct gtgaatgcaa tcagcgattc    1440
ccaagtgaag atgcagtaga aaagcatgtt ttctcagcaa acacaatggg ttataaatgt    1500
```

```
gtggtctgtg gaaaggtatg tgatgattca ggggtcattc gtttacacat gagccggatt    1560
cacggagggg cacatttaaa taactttctt ttctggtgtc ggacatgcaa aaaggagtta    1620
acaaggaaag atactatcat ggcacatgtg actgaatttc ataatggaca cagatatttt    1680
tatgagatgg atgaggtaga aggtgaaact ttgccatcat cctctacaac attggataat    1740
ttgactgcta acaagccttc atcagctatt actgttattg atcattcccc ggcaaatagt    1800
tctccgaggg gtaaatggca atgccggatt tgtgaagata tgtttgattc ccaggaatat    1860
gtaaaacagc actgcatgtc tttggcaagc cacaagtttc atagatacag ctgtgctcac    1920
tgcagaaagc cttttcataa gatagaaaca ttgtaccgac attgccaaga tgagcatgac    1980
aatgagataa agattaaata cttctgtggg ctttgtgatc ttatctttaa tgtggaagaa    2040
gcatttctga gtcattatga ggagcaccac agcatagatt atgtatttgt gtcagaaaaa    2100
actgaaactt caattaaaac cgaagatgat tttccagtaa tagagaccag taaccagtta    2160
acttgtggtt gccgtgagag ttacatctgt aaagtcaaca gaaaagaaga ttatagcaga    2220
tgtctccaaa tcatgctgga taaggaaaa ctgtggtttc gctgcagttt atgttcggca    2280
acagcacaga atttaaccga catgaacact catatccatc aagtgcacaa agaaaagagt    2340
gatgaggagg agcagcagta tgtaatcaag tgtggcacct gcaccaaagc atttcatgat    2400
cctgagagtg cacagcagca tttccataga aaacattgct tcttacagaa acccagtgtg    2460
gctcattttg gatctgaaaa atcaaacctg tacaagttta ctgctagtgc ctcacataca    2520
gagagaaaac tgaaacaggc aataaactat tcaaaaagtt tagacatgga aaaggagtt    2580 gagaatgacc taagctatca gaatatagga ggaaacacca attggaagcc tccgctcaac    2640
tgtaagattt ataactacct gaacaggatt ggatgcttct tccttcatcc tcgctgtagt    2700
aaaagaaaag atgctgctga ttttgccata tgtatgcatg ctggccgtct agatgaacaa    2760
ctacccaagc aaaattcctt caccatcctc tcaggagatc aaggttttct ggagctagag    2820
aatcaattta agaagactca gaggccagct catatactaa accctcacca cttagaggga    2880
gatatgatgt gtgccttgtt aaatagcata tctgatacca ccaaagaatg tgacagtgat    2940
gataacatgg gtgccaaaaa tacttcaata ggagaagaat ttatatccac agaagatgtg    3000
gaattagaag aagctattag aagaagtctt gaggaaatgt aa                       3042

<210> SEQ ID NO 6
<211> LENGTH: 3042
<212> TYPE: DNA
<213> ORGANISM: Homo sapiens

<400> SEQUENCE: 6
atgggagacc cggggtcgga gataatagaa tctgtccctc cagctggccc tgaggcatct     60
gagtcaacaa cggatgaaaa tgaagacgac attcagtttg tcagtgaagg accattacga    120
cctgttcttg aatacattga tctggtcagc agtgatgatg aagagcctag cacctcttat    180
actgatgaga atattaaacg taaagaccat attgattatc agaaggataa agttgcttta    240
actctggctc gtctagcccg ccatgttgaa gtggagaaac agcagaaaga agagaagaat    300
agagcattca gagaaaaaat tgattttcag catgctcatg ggttacaaga attggaattt    360
attcgaggac attctgatac agaagcagca agactgtgtg tggaccagtg gctaaaaatg    420
ccaggactca aaacaggcac aattaattgt ggaacaaaaa gttcattccg aagaggaggc    480
cacacgtggg tgtctgggaa accaactta tgtcctataa tgcactgtaa caaggagttt    540
```

```
gacaatgggc accttctctt aggacatttg aaaaggttcg atcactctcc atgtgatcca    600
acaattacac tacatggacc tttcttcagc tcctttgctt gtgtagtatg ttataaaaaa    660
tttgttactc aacaacaata tagagatcac cttttgata aggaagccac agatgatgga    720
cataacaaca accttcttcc tcagattatt cagtgttttg catgtccaaa ttgcttcctt    780
cttttagca gaaggagga gtgttcaaag catatgtctg aaagaatca tttccatcag      840
agtttcaaac tgggtgataa caaggaatt gcacatccaa tatctttccc atcttttgca    900
aagaaacttt tgatctctct gtgcaaagat gttcccttc aagttaagtg tgtggcctgc    960
cacaagacac tgcgttccca catggagctc actgcccatt tcagagttca ttgtcgaaat   1020
gctggacctg tagctgtagc tgagaagagc attacccagg ttgcagagaa attcatatta   1080
agaggttatt gtccagattg caatcaagtc tttgtggatg aaaccagcac ccaaaatcat   1140
aagcagaatt caggacacaa agtccgagtc attaactcag tggaagaatc agtcttactc   1200
tattgccaca gcagcgaagg gaacaaggat ccttcttctg acttgcattt attgttggat   1260
caatcaaaat tttcatcact taaaagaacc atgtctatta agaatctag ctcactggag    1320
tgcattgcca ttccaaaaaa gaagatgaat ttaaaagata aagccatga aggtgttgct    1380
tgtgtccaga agaaaaatc agtagttaaa acctggttct gtgaatgcaa tcagcgattc    1440
ccaagtgaag atgcagtaga aaagcatgtt ttctcagcaa acacaatggg ttataaatgt   1500
gtggtctgtg gaaaggtatg tgatgattca ggggtcattc gtttacacat gagccggatt   1560
cacggagggg cacatttaaa taactttctt ttctggtgtc ggacatgcaa aaaggagtta   1620
acaaggaaag atactatcat ggcacatgtg actgaatttc ataatggaca cagatatttt   1680
tatgagatgg atgaggtaga aggtgaaact ttgccatcat cctctacaac attggataat   1740
ttgactgcta acaagccttc atcagctatt actgttattg atcattcccc ggcaaatagt   1800
tctccgaggg gtaaatggca atgccggatt tgtgaagata tgtttgattc caggaatat    1860
gtaaaacagc actgcatgtc tttggcaagc cacaagtttc atagatacag ctgtgctcac   1920
tgcagaaagc cttttcataa gatagaaaca ttgtaccgac attgccaaga tgagcatgac   1980
aatgagataa agattaaata cttctgtggg ctttgtgatc ttatctttaa tgtggaagaa   2040
gcatttctga gtcattatga ggagcaccac agcatagatt atgtatttgt gtcagaaaaa   2100
actgaaactt caattaaaac cgaagatgat tttccagtaa tagagaccag taaccagtta   2160
acttgtggtt gccgtgagag ttacatctgt aaagtcaaca gaaaagaaga ttatagcaga   2220
tgtctccaaa tcatgctgga taaggaaaa ctgtggtttc gctgcagttt atgttcggca    2280
acagcacaga atttaaccga catgaacact catatccatc aagtgcacaa agaaaagagt   2340
gatgaggagg agcagcagta tgtaatcaag tgtggcacct gcaccaaagc atttcatgat   2400
cctgagagtg cacagcagca tttccataga aaacattgct tcttacagaa acccagtgtg   2460
gctcattttg gatctgaaaa atcaaacctg tacaagttta ctgctagtgc ctcacataca   2520
gagagaaaac tgaaacaggc aataaactat tcaaaagtt tagacatgga gaaggagtt    2580
gagaatgacc taagctatca gaatatagga ggaaacacca attggaagcc tccgctcaac   2640
tgtaagattt ataactacct gaacaggatt ggatgcttct tccttcatcc tcgctgtagt   2700
aaaagaaaag atgctgctga ttttgccata tgtatgcatg ctggccgtct agatgaacaa   2760
ctacccaagc aaattccttt caccatcctc tcaggagatc aaggttttct ggagctagag   2820
aatcaattta agaagactca gaggccagct catatactaa accctcacca cttagaggga   2880
gatatgatgt gtgccttgtt aaatagcata tctgatacca ccaaagaatg tgacagtgat   2940
```

-continued

```
gataacatgg gtgccaaaaa tacttcaata ggagaagaat ttatatccac agaagatgtg    3000
gaattagaag aagctattag aagaagtctt gaggaaatgt aa                       3042
```

<210> SEQ ID NO 7
<211> LENGTH: 1013
<212> TYPE: PRT
<213> ORGANISM: Homo sapiens

<400> SEQUENCE: 7

```
Met Gly Asp Pro Gly Ser Glu Ile Ile Glu Ser Val Pro Ala Gly
  1               5                  10                  15

Pro Glu Ala Ser Glu Ser Thr Thr Asp Glu Asn Glu Asp Ile Gln
                 20                  25                  30

Phe Val Ser Glu Gly Pro Leu Arg Pro Val Leu Glu Tyr Ile Asp Leu
         35                  40                  45

Val Ser Asp Asp Glu Glu Pro Ser Thr Ser Tyr Thr Asp Glu Asn
     50                  55                  60

Ile Lys Arg Lys Asp His Ile Asp Tyr Gln Lys Asp Lys Val Ala Leu
 65                  70                  75                  80

Thr Leu Ala Arg Leu Ala Arg His Val Glu Val Lys Gln Gln Lys
                 85                  90                  95

Glu Glu Lys Asn Arg Ala Phe Arg Glu Lys Ile Asp Phe Gln His Ala
                100                 105                 110

His Gly Leu Gln Glu Leu Glu Phe Ile Arg Gly His Ser Asp Thr Glu
            115                 120                 125

Ala Ala Arg Leu Cys Val Asp Gln Trp Leu Lys Met Pro Gly Leu Lys
        130                 135                 140

Thr Gly Thr Ile Asn Cys Gly Thr Lys Ser Ser Phe Arg Arg Gly Gly
145                 150                 155                 160

His Thr Trp Val Ser Gly Lys Pro Ile Leu Cys Pro Ile Met His Cys
                165                 170                 175

Asn Lys Glu Phe Asp Asn Gly His Leu Leu Leu Gly His Leu Lys Arg
            180                 185                 190

Phe Asp His Ser Pro Cys Asp Pro Thr Ile Thr Leu His Gly Pro Phe
        195                 200                 205

Phe Ser Ser Phe Ala Cys Val Val Cys Tyr Lys Lys Phe Val Thr Gln
    210                 215                 220

Gln Gln Tyr Arg Asp His Leu Phe Asp Lys Glu Ala Thr Asp Gly
225                 230                 235                 240

His Asn Asn Leu Leu Pro Gln Ile Ile Gln Cys Phe Ala Cys Pro
                245                 250                 255

Asn Cys Phe Leu Leu Phe Ser Arg Lys Glu Glu Cys Ser Lys His Met
            260                 265                 270

Ser Gly Lys Asn His Phe His Gln Ser Phe Lys Leu Gly Asp Asn Lys
        275                 280                 285

Gly Ile Ala His Pro Ile Ser Phe Pro Ser Phe Ala Lys Lys Leu Leu
    290                 295                 300

Ile Ser Leu Cys Lys Asp Val Pro Phe Gln Val Lys Cys Val Ala Cys
305                 310                 315                 320

His Lys Thr Leu Arg Ser His Met Glu Leu Thr Ala His Phe Arg Val
                325                 330                 335

His Cys Arg Asn Ala Gly Pro Val Ala Val Ala Glu Lys Ser Ile Thr
            340                 345                 350
```

-continued

```
Gln Val Ala Glu Lys Phe Ile Leu Arg Gly Tyr Cys Pro Asp Cys Asn
        355                 360                 365
Gln Val Phe Val Asp Glu Thr Ser Thr Gln Asn His Lys Gln Asn Ser
        370                 375                 380
Gly His Lys Val Arg Val Ile Asn Ser Val Glu Ser Val Leu Leu
385                 390                 395                 400
Tyr Cys His Ser Ser Glu Gly Asn Lys Asp Pro Ser Ser Asp Leu His
                    405                 410                 415
Leu Leu Leu Asp Gln Ser Lys Phe Ser Ser Leu Lys Arg Thr Met Ser
            420                 425                 430
Ile Lys Glu Ser Ser Ser Leu Glu Cys Ile Ala Ile Pro Lys Lys Lys
        435                 440                 445
Met Asn Leu Lys Asp Lys Ser His Glu Gly Val Ala Cys Val Gln Lys
    450                 455                 460
Glu Lys Ser Val Val Lys Thr Trp Phe Cys Glu Cys Asn Gln Arg Phe
465                 470                 475                 480
Pro Ser Glu Asp Ala Val Glu Lys His Val Phe Ser Ala Asn Thr Met
                    485                 490                 495
Gly Tyr Lys Cys Val Val Cys Gly Lys Val Cys Asp Asp Ser Gly Val
                500                 505                 510
Ile Arg Leu His Met Ser Arg Ile His Gly Gly Ala His Leu Asn Asn
        515                 520                 525
Phe Leu Phe Trp Cys Arg Thr Cys Lys Lys Glu Leu Thr Arg Lys Asp
    530                 535                 540
Thr Ile Met Ala His Val Thr Glu Phe His Asn Gly His Arg Tyr Phe
545                 550                 555                 560
Tyr Glu Met Asp Glu Val Glu Gly Glu Thr Leu Pro Ser Ser Ser Thr
                    565                 570                 575
Thr Leu Asp Asn Leu Thr Ala Asn Lys Pro Ser Ser Ala Ile Thr Val
            580                 585                 590
Ile Asp His Ser Pro Ala Asn Ser Ser Pro Arg Gly Lys Trp Gln Cys
        595                 600                 605
Arg Ile Cys Glu Asp Met Phe Asp Ser Gln Glu Tyr Val Lys Gln His
    610                 615                 620
Cys Met Ser Leu Ala Ser His Lys Phe His Arg Tyr Ser Cys Ala His
625                 630                 635                 640
Cys Arg Lys Pro Phe His Lys Ile Glu Thr Leu Tyr Arg His Cys Gln
                    645                 650                 655
Asp Glu His Asp Asn Glu Ile Lys Ile Lys Tyr Phe Cys Gly Leu Cys
            660                 665                 670
Asp Leu Ile Phe Asn Val Glu Glu Ala Phe Leu Ser His Tyr Glu Glu
        675                 680                 685
His His Ser Ile Asp Tyr Val Phe Val Ser Lys Thr Glu Thr Ser
    690                 695                 700
Ile Lys Thr Glu Asp Asp Phe Pro Val Ile Glu Thr Ser Asn Gln Leu
705                 710                 715                 720
Thr Cys Gly Cys Arg Glu Ser Tyr Ile Cys Lys Val Asn Arg Lys Glu
                    725                 730                 735
Asp Tyr Ser Arg Cys Leu Gln Ile Met Leu Asp Lys Gly Lys Leu Trp
            740                 745                 750
Phe Arg Cys Ser Leu Cys Ser Ala Thr Ala Gln Asn Leu Thr Asp Met
        755                 760                 765
```

```
Asn Thr His Ile His Gln Val His Lys Glu Lys Ser Asp Glu Glu Glu
    770                 775                 780

Gln Gln Tyr Val Ile Lys Cys Gly Thr Cys Thr Lys Ala Phe His Asp
785                 790                 795                 800

Pro Glu Ser Ala Gln Gln His Phe His Arg Lys His Cys Phe Leu Gln
                805                 810                 815

Lys Pro Ser Val Ala His Phe Gly Ser Glu Lys Ser Asn Leu Tyr Lys
                820                 825                 830

Phe Thr Ala Ser Ala Ser His Thr Glu Arg Lys Leu Lys Gln Ala Ile
                835                 840                 845

Asn Tyr Ser Lys Ser Leu Asp Met Glu Lys Gly Val Glu Asn Asp Leu
850                 855                 860

Ser Tyr Gln Asn Ile Gly Gly Asn Thr Asn Trp Lys Pro Pro Leu Asn
865                 870                 875                 880

Cys Lys Ile Tyr Asn Tyr Leu Asn Arg Ile Gly Cys Phe Phe Leu His
                885                 890                 895

Pro Arg Cys Ser Lys Arg Lys Asp Ala Ala Asp Phe Ala Ile Cys Met
                900                 905                 910

His Ala Gly Arg Leu Asp Glu Gln Leu Pro Lys Gln Ile Pro Phe Thr
                915                 920                 925

Ile Leu Ser Gly Asp Gln Gly Phe Leu Glu Leu Glu Asn Gln Phe Lys
                930                 935                 940

Lys Thr Gln Arg Pro Ala His Ile Leu Asn Pro His His Leu Glu Gly
945                 950                 955                 960

Asp Met Met Cys Ala Leu Leu Asn Ser Ile Ser Asp Thr Thr Lys Glu
                965                 970                 975

Cys Asp Ser Asp Asp Asn Met Gly Ala Lys Asn Thr Ser Ile Gly Glu
                980                 985                 990

Glu Phe Ile Ser Thr Glu Asp Val Glu Leu Glu Ala Ile Arg Arg
                995             1000                1005

Ser Leu Glu Glu Met
    1010

<210> SEQ ID NO 8
<211> LENGTH: 1013
<212> TYPE: PRT
<213> ORGANISM: Homo sapiens

<400> SEQUENCE: 8

Met Gly Asp Pro Gly Ser Glu Ile Ile Glu Ser Val Pro Pro Ala Gly
1               5                   10                  15

Pro Glu Ala Ser Glu Ser Thr Thr Asp Glu Asn Glu Asp Asp Ile Gln
                20                  25                  30

Phe Val Ser Glu Gly Pro Leu Arg Pro Val Leu Glu Tyr Ile Asp Leu
            35                  40                  45

Val Ser Ser Asp Asp Glu Glu Pro Ser Thr Ser Tyr Thr Asp Glu Asn
    50                  55                  60

Ile Lys Arg Lys Asp His Ile Asp Tyr Gln Lys Asp Lys Val Ala Leu
65                  70                  75                  80

Thr Leu Ala Arg Leu Ala Arg His Val Glu Val Glu Lys Gln Gln Lys
                85                  90                  95

Glu Glu Lys Asn Arg Ala Phe Arg Glu Lys Ile Asp Phe Gln His Ala
                100                 105                 110
```

```
His Gly Leu Gln Glu Leu Glu Phe Ile Arg Gly His Ser Asp Thr Glu
        115                 120                 125

Ala Ala Arg Leu Cys Val Asp Gln Trp Leu Lys Met Pro Gly Leu Lys
130                 135                 140

Thr Gly Thr Ile Asn Cys Gly Thr Lys Ser Ser Phe Arg Arg Gly Gly
145                 150                 155                 160

His Thr Trp Val Ser Gly Lys Pro Thr Leu Cys Pro Ile Met His Cys
                165                 170                 175

Asn Lys Glu Phe Asp Asn Gly His Leu Leu Leu Gly His Leu Lys Arg
            180                 185                 190

Phe Asp His Ser Pro Cys Asp Pro Thr Ile Thr Leu His Gly Pro Phe
        195                 200                 205

Phe Ser Ser Phe Ala Cys Val Cys Tyr Lys Lys Phe Val Thr Gln
210                 215                 220

Gln Gln Tyr Arg Asp His Leu Phe Asp Lys Glu Ala Thr Asp Gly
225                 230                 235                 240

His Asn Asn Leu Leu Pro Gln Ile Ile Gln Cys Phe Ala Cys Pro
            245                 250                 255

Asn Cys Phe Leu Leu Phe Ser Arg Lys Glu Glu Cys Ser Lys His Met
            260                 265                 270

Ser Gly Lys Asn His Phe His Gln Ser Phe Lys Leu Gly Asp Asn Lys
        275                 280                 285

Gly Ile Ala His Pro Ile Ser Phe Pro Ser Phe Ala Lys Lys Leu Leu
290                 295                 300

Ile Ser Leu Cys Lys Asp Val Pro Phe Gln Val Lys Cys Val Ala Cys
305                 310                 315                 320

His Lys Thr Leu Arg Ser His Met Glu Leu Thr Ala His Phe Arg Val
                325                 330                 335

His Cys Arg Asn Ala Gly Pro Val Ala Val Ala Glu Lys Ser Ile Thr
            340                 345                 350

Gln Val Ala Glu Lys Phe Ile Leu Arg Gly Tyr Cys Pro Asp Cys Asn
        355                 360                 365

Gln Val Phe Val Asp Glu Thr Ser Thr Gln Asn His Lys Gln Asn Ser
370                 375                 380

Gly His Lys Val Arg Val Ile Asn Ser Val Glu Glu Ser Val Leu Leu
385                 390                 395                 400

Tyr Cys His Ser Ser Glu Gly Asn Lys Asp Pro Ser Ser Asp Leu His
                405                 410                 415

Leu Leu Leu Asp Gln Ser Lys Phe Ser Ser Leu Lys Arg Thr Met Ser
            420                 425                 430

Ile Lys Glu Ser Ser Ser Leu Glu Cys Ile Ala Ile Pro Lys Lys Lys
        435                 440                 445

Met Asn Leu Lys Asp Lys Ser His Glu Gly Val Ala Cys Val Gln Lys
        450                 455                 460

Glu Lys Ser Val Val Lys Thr Trp Phe Cys Glu Cys Asn Gln Arg Phe
465                 470                 475                 480

Pro Ser Glu Asp Ala Val Glu Lys His Val Phe Ser Ala Asn Thr Met
                485                 490                 495

Gly Tyr Lys Cys Val Val Cys Gly Lys Val Cys Asp Asp Ser Gly Val
                500                 505                 510

Ile Arg Leu His Met Ser Arg Ile His Gly Gly Ala His Leu Asn Asn
            515                 520                 525
```

-continued

```
Phe Leu Phe Trp Cys Arg Thr Cys Lys Lys Glu Leu Thr Arg Lys Asp
    530                 535                 540

Thr Ile Met Ala His Val Thr Glu Phe His Asn Gly His Arg Tyr Phe
545                 550                 555                 560

Tyr Glu Met Asp Glu Val Glu Gly Glu Thr Leu Pro Ser Ser Ser Thr
                565                 570                 575

Thr Leu Asp Asn Leu Thr Ala Asn Lys Pro Ser Ser Ala Ile Thr Val
            580                 585                 590

Ile Asp His Ser Pro Ala Asn Ser Ser Pro Arg Gly Lys Trp Gln Cys
        595                 600                 605

Arg Ile Cys Glu Asp Met Phe Asp Ser Gln Glu Tyr Val Lys Gln His
    610                 615                 620

Cys Met Ser Leu Ala Ser His Lys Phe His Arg Tyr Ser Cys Ala His
625                 630                 635                 640

Cys Arg Lys Pro Phe His Lys Ile Glu Thr Leu Tyr Arg His Cys Gln
                645                 650                 655

Asp Glu His Asp Asn Glu Ile Lys Ile Lys Tyr Phe Cys Gly Leu Cys
            660                 665                 670

Asp Leu Ile Phe Asn Val Glu Glu Ala Phe Leu Ser His Tyr Glu Glu
        675                 680                 685

His His Ser Ile Asp Tyr Val Phe Val Ser Glu Lys Thr Glu Thr Ser
    690                 695                 700

Ile Lys Thr Glu Asp Asp Phe Pro Val Ile Glu Thr Ser Asn Gln Leu
705                 710                 715                 720

Thr Cys Gly Cys Arg Glu Ser Tyr Ile Cys Lys Val Asn Arg Lys Glu
                725                 730                 735

Asp Tyr Ser Arg Cys Leu Gln Ile Met Leu Asp Lys Gly Lys Leu Trp
            740                 745                 750

Phe Arg Cys Ser Leu Cys Ser Ala Thr Ala Gln Asn Leu Thr Asp Met
        755                 760                 765

Asn Thr His Ile His Gln Val His Lys Glu Lys Ser Asp Glu Glu Glu
    770                 775                 780

Gln Gln Tyr Val Ile Lys Cys Gly Thr Cys Thr Lys Ala Phe His Asp
785                 790                 795                 800

Pro Glu Ser Ala Gln Gln His Phe Arg Lys His Cys Phe Leu Gln
                805                 810                 815

Lys Pro Ser Val Ala His Phe Gly Ser Glu Lys Ser Asn Leu Tyr Lys
            820                 825                 830

Phe Thr Ala Ser Ala Ser His Thr Glu Arg Lys Leu Lys Gln Ala Ile
        835                 840                 845

Asn Tyr Ser Lys Ser Leu Asp Met Glu Lys Gly Val Glu Asn Asp Leu
    850                 855                 860

Ser Tyr Gln Asn Ile Gly Gly Asn Thr Asn Trp Lys Pro Pro Leu Asn
865                 870                 875                 880

Cys Lys Ile Tyr Asn Tyr Leu Asn Arg Ile Gly Cys Phe Phe Leu His
                885                 890                 895

Pro Arg Cys Ser Lys Arg Lys Asp Ala Ala Asp Phe Ala Ile Cys Met
            900                 905                 910

His Ala Gly Arg Leu Asp Glu Gln Leu Pro Lys Gln Ile Pro Phe Thr
        915                 920                 925

Ile Leu Ser Gly Asp Gln Gly Phe Leu Glu Leu Glu Asn Gln Phe Lys
    930                 935                 940
```

-continued

Lys Thr Gln Arg Pro Ala His Ile Leu Asn Pro His His Leu Glu Gly
945                 950                 955                 960

Asp Met Met Cys Ala Leu Leu Asn Ser Ile Ser Asp Thr Thr Lys Glu
                965                 970                 975

Cys Asp Ser Asp Asp Asn Met Gly Ala Lys Asn Thr Ser Ile Gly Glu
            980                 985                 990

Glu Phe Ile Ser Thr Glu Asp Val Glu Leu Glu Ala Ile Arg Arg
        995                 1000                1005

Ser Leu Glu Glu Met
    1010

<210> SEQ ID NO 9
<211> LENGTH: 3183
<212> TYPE: DNA
<213> ORGANISM: Homo sapiens

<400> SEQUENCE: 9

| | | |
|---|---|---|
| atgggagacc cggggtcgga gataatagaa tctgtccctc cagctggccc tgaggcatct | 60 |
| gagtcaacaa cggatgaaaa tgaagacgac attcagtttg tcagtgaagg accattacga | 120 |
| cctgttcttg aatacattga tctggtcagc agtgatgatg aagagcctag cacctcttat | 180 |
| actgatgaga atattaaacg taaagaccat attgattatc agaaggataa agttgcttta | 240 |
| actctggctc gtctagcccg ccatgttgaa gtggagaaac agcagaaaga gagaagaat | 300 |
| agagcattca gagaaaaaat tgattttcag catgctcatg gttacaagaa ttggaatttt | 360 |
| attcgaggac attctgatac agaagcagca agactgtgtg tggaccagtg gctaaaaatg | 420 |
| ccaggactca aaacaggcac aattaattgt ggaacaaaaa gttcattccg aagaggaggc | 480 |
| cacacgtggg tgtctgggaa accaatttta tgtcctataa tgcactgtaa caaggagttt | 540 |
| gacaatgggc accttctctt aggacatttg aaaaggttcg atcactctcc atgtgatcca | 600 |
| acaattacac tacatggacc tttcttcagc tcctttgctt gtgtagtatg ttataaaaaa | 660 |
| tttgttactc aacaacaata tagagatcac cttttttgata aggaagccac agatgatgga | 720 |
| cataacaaca accttcttcc tcagattatt cagtgttttg catgtccaaa ttgcttcctt | 780 |
| cttttttagca gaaaggagga gtgttcaaag catatgtctg aaagaatca tttccatcag | 840 |
| agttcaaac tgggtgataa caaaggaatt gcacatccaa tatctttccc atcttttgca | 900 |
| aagaaacttt tgatctctct gtgcaaagat gttccctttc aagttaagtg tgtggcctgc | 960 |
| cacaagacac tgcgttccca catggagctc actgcccatt tcagagttca ttgtcgaaat | 1020 |
| gctggacctg tagctgtagc tgagaagagc attacccagg ttgcagagaa attcatatta | 1080 |
| agaggttatt gtccagattg caatcaagtc tttgtggata aaaccagcac ccaaaatcat | 1140 |
| aagcagaatt caggacacaa agtccgagtc attaactcag tggaagaatc agtcttactc | 1200 |
| tattgccaca gcagcgaagg gaacaaggat ccttcttctg acttgcattt attgttggat | 1260 |
| caatcaaaat tttcatcact taaagaacc atgtctatta agaatctag ctcactggag | 1320 |
| tgcattgcca ttccaaaaaa gaagatgaat ttaaaagata aagccatga aggtgttgct | 1380 |
| tgtgtccaga agaaaaatc agtagttaaa acctggttct gtgaatgcaa tcagcgattc | 1440 |
| ccaagtgaag atgcagtaga aaagcatgtt ttctcagcaa acacaatggg ttataaatgt | 1500 |
| gtggtctgtg aaaggtatg tgatgattca ggggtcattc gtttacacat gagccggatt | 1560 |
| cacgaggggg cacatttaaa taactttctt tctggtgtc ggacatgcaa aaaggagtta | 1620 |
| acaaggaaag atactatcat ggcacatgtg actgaatttc ataatggaca cagatatttt | 1680 |

```
tatgagatgg atgaggtaga aggtgaaact ttgccatcat cctctacaac attggataat    1740
ttgactgcta acaagccttc atcagctatt actgttattg atcattcccc ggcaaatagt    1800
tctccgaggg gtaaatggca atgccggatt tgtgaagata tgtttgattc caggaatat     1860
gtaaaacagc actgcatgtc tttggcaagc cacaagtttc atagatacag ctgtgctcac    1920
tgcagaaagc cttttcataa gatagaaaca ttgtaccgac attgccaaga tgagcatgac    1980
aatgagataa agattaaata cttctgtggg ctttgtgatc ttatctttaa tgtggaagaa    2040
gcatttctga gtcattatga ggagcaccac agcatagatt atgtatttgt gtcagaaaaa    2100
actgaaactt caattaaaac cgaagatgat tttccagtaa tagagaccag taaccagtta    2160
acttgtggtt gccgtgagag ttacatctgt aaagtcaaca gaaaagaaga ttatagcaga    2220
tgtctccaaa tcatgctgga taaaggaaaa ctgtggtttc gctgcagttt atgttcggca    2280
acagcacaga atttaaccga catgaacact catatccatc aagtgcacaa agaaaagagt    2340
gatgaggagg agcagcagta tgtaatcaag tgtggcacct gcaccaaagc atttcatgat    2400
cctgagagtg cacagcagca tttccataga aaacattgct tcttacagaa acccagtgtg    2460
gctcattttg gatctgaaaa atcaaacctg tacaagttta ctgctagtgc ctcacataca    2520
gagagaaaac tgaaacaggc aataaactat tcaaaaagtt tagacatgga aaaggagtt    2580
gagaatgacc taagctatca gaatatagag gaagaaattg ttgagcttcc agatttggat    2640
tacctgcgaa ccatgactca tatagtcttt gtagattttg ataactggtc aaactttttt    2700
ggtcatctac cagggcatct aaaccaagga acatttattt ggggctttca aggaggaaac    2760
accaattgga agcctccgct caactgtaag atttataact acctgaacag gattggatgc    2820
ttcttccttc atcctcgctg tagtaaaaga aaagatgctg ctgattttgc catatgtatg    2880
catgctggcc gtctagatga acaactaccc aagcaaattc ctttcaccat cctctcagga    2940
gatcaaggtt ttctggagct agagaatcaa tttaagaaga ctcagaggcc agctcatata    3000
ctaaaccctc accacttaga gggagatatg atgtgtgcct tgttaaatag catatctgat    3060
accaccaaag aatgtgacag tgatgataac atgggtgcca aaaatacttc aataggagaa    3120
gaatttatat ccacagaaga tgtggaatta aagaagcta ttagaagaag tcttgaggaa    3180
atg                                                                   3183

<210> SEQ ID NO 10
<211> LENGTH: 3183
<212> TYPE: DNA
<213> ORGANISM: Homo sapiens

<400> SEQUENCE: 10
atgggagacc cggggtcgga gataatagaa tctgtccctc cagctggccc tgaggcatct      60
gagtcaacaa cggatgaaaa tgaagacgac attcagtttg tcagtgaagg accattacga    120
cctgttcttg aatacattga tctggtcagc agtgatgatg aagagcctag cacctcttat    180
actgatgaga atattaaacg taaagaccat attgattatc agaaggataa agttgcttta    240
actctggctc gtctagcccg ccatgttgaa gtggagaaac agcagaaaga agagaagaat    300
agagcattca gagaaaaaat tgattttcag catgctcatg ggttacaaga attggaattt    360
attcgaggac attctgatac agaagcagca agactgtgtg tggaccagtg gctaaaaatg    420
ccaggactca aaacaggcac aattaattgt ggaacaaaaa gttcattccg aagaggaggc    480
cacacgtggg tgtctgggaa accaacttta tgtcctataa tgcactgtaa caaggagttt    540
```

```
gacaatgggc accttctctt aggacatttg aaaaggttcg atcactctcc atgtgatcca      600
acaattacac tacatggacc tttcttcagc tcctttgctt gtgtagtatg ttataaaaaa      660
tttgttactc aacaacaata tagagatcac cttttttgata aggaagccac agatgatgga     720
cataacaaca accttcttcc tcagattatt cagtgttttg catgtccaaa ttgcttcctt      780 cttttttagca gaaaggagga gtgttcaaag catatgtctg gaaagaatca tttccatcag     840
agtttcaaac tgggtgataa caaaggaatt gcacatccaa tatctttccc atcttttgca      900
aagaaacttt tgatctctct gtgcaaagat gttccctttc aagttaagtg tgtggcctgc      960
cacaagacac tgcgttccca catggagctc actgccatt tcagagttca ttgtcgaaat      1020
gctggacctg tagctgtagc tgagaagagc attacccagg ttgcagagaa attcatatta    1080
agaggttatt gtccagattg caatcaagtc tttgtggatg aaaccagcac ccaaaatcat    1140
aagcagaatt caggacacaa agtccgagtc attaactcag tggaagaatc agtcttactc   1200
tattgccaca gcagcgaagg gaacaaggat ccttcttctg acttgcattt attgttggat   1260
caatcaaaat tttcatcact taaaagaacc atgtctatta agaatctag ctcactggag    1320 tgcattgcca ttccaaaaaa gaagatgaat ttaaaagata aaagccatga aggtgttgct   1380
tgtgtccaga aagaaaaatc agtagttaaa acctggttct gtgaatgcaa tcagcgattc   1440
ccaagtgaag atgcagtaga aaagcatgtt ttctcagcaa acacaatggg ttataaatgt   1500
gtggtctgtg gaaaggtatg tgatgattca ggggtcattc gtttacacat gagccggatt   1560
cacggagggg cacatttaaa taactttctt ttctggtgtc ggacatgcaa aaaggagtta   1620
acaaggaaag atactatcat ggcacatgtg actgaatttc ataatggaca cagatatttt   1680
tatgagatgg atgaggtaga aggtgaaact ttgccatcat cctctacaac attggataat   1740
ttgactgcta acaagccttc atcagctatt actgttattg atcattcccc ggcaaatagt   1800
tctccgaggg gtaaatggca atgccggatt tgtgaagata tgtttgattc ccaggaatat   1860
gtaaaacagc actgcatgtc tttggcaagc cacaagtttc atagatacag ctgtgctcac   1920
tgcagaaagc cttttcataa gatagaaaca ttgtaccgac attgccaaga tgagcatgac   1980
aatgagataa agattaaata cttctgtggg ctttgtgatc ttatctttaa tgtggaagaa   2040
gcatttctga gtcattatga ggagcaccac agcatagatt atgtatttgt gtcagaaaaa   2100
actgaaactt caattaaaac cgaagatgat tttccagtaa tagagaccag taaccagtta   2160
acttgtggtt gccgtgagag ttacatctgt aaagtcaaca gaaaagaaga ttatagcaga   2220
tgtctccaaa tcatgctgga taaggaaaa ctgtggtttc gctgcagttt atgttcggca    2280
acagcacaga atttaaccga catgaacact catatccatc aagtgcacaa agaaaagagt   2340
gatgaggagg agcagcagta tgtaatcaag tgtggcacct gcaccaaagc atttcatgat   2400
cctgagagtg cacagcagca tttccataga aaacattgct tcttacagaa acccagtgtg   2460
gctcattttg gatctgaaaa atcaaacctg tacaagttta ctgctagtgc ctcacataca    2520
gagagaaaac tgaaacaggc aataaactat tcaaaaagtt tagacatgga gaaggagtt    2580 gagaatgacc taagctatca gaatatagag gaagaaattt tgagcttcc agatttggat   2640 tacctgcgaa ccatgactca tatagtcttt gtagattttg ataactggtc aaactttttt   2700
ggtcatctac cagggcatct aaaccaagga acatttattt ggggctttca aggaggaaac   2760
accaattgga agcctccgct caactgtaag atttataact acctgaacag gattggatgc   2820
ttcttccttc atcctcgctg tagtaaaaga aaagatgctg ctgattttgc catatgtatg   2880
catgctggcc gtctagatga acaactaccc aagcaaattc cttcaccat cctctcagga   2940
```

```
gatcaaggtt tctggagct agagaatcaa tttaagaaga ctcagaggcc agctcatata    3000
ctaaaccctc accacttaga gggagatatg atgtgtgcct tgttaaatag catatctgat    3060
accaccaaag aatgtgacag tgatgataac atgggtgcca aaaatacttc aataggagaa    3120
gaatttatat ccacagaaga tgtggaatta gaagaagcta ttagaagaag tcttgaggaa    3180
atg                                                                  3183
```

<210> SEQ ID NO 11
<211> LENGTH: 1061
<212> TYPE: PRT
<213> ORGANISM: Homo sapiens

<400> SEQUENCE: 11

```
Met Gly Asp Pro Gly Ser Glu Ile Ile Glu Ser Val Pro Pro Ala Gly
 1               5                  10                  15

Pro Glu Ala Ser Glu Ser Thr Thr Asp Glu Asn Glu Asp Asp Ile Gln
             20                  25                  30

Phe Val Ser Glu Gly Pro Leu Arg Pro Val Leu Glu Tyr Ile Asp Leu
         35                  40                  45

Val Ser Ser Asp Asp Glu Glu Pro Ser Thr Ser Tyr Thr Asp Glu Asn
     50                  55                  60

Ile Lys Arg Lys Asp His Ile Asp Tyr Gln Lys Asp Lys Val Ala Leu
 65                  70                  75                  80

Thr Leu Ala Arg Leu Ala Arg His Val Glu Val Glu Lys Gln Gln Lys
                 85                  90                  95

Glu Glu Lys Asn Arg Ala Phe Arg Glu Lys Ile Asp Phe Gln His Ala
            100                 105                 110

His Gly Leu Gln Glu Leu Glu Phe Ile Arg Gly His Ser Asp Thr Glu
        115                 120                 125

Ala Ala Arg Leu Cys Val Asp Gln Trp Leu Lys Met Pro Gly Leu Lys
    130                 135                 140

Thr Gly Thr Ile Asn Cys Gly Thr Lys Ser Ser Phe Arg Arg Gly Gly
145                 150                 155                 160

His Thr Trp Val Ser Gly Lys Pro Ile Leu Cys Pro Ile Met His Cys
                165                 170                 175

Asn Lys Glu Phe Asp Asn Gly His Leu Leu Gly His Leu Lys Arg
            180                 185                 190

Phe Asp His Ser Pro Cys Asp Pro Thr Ile Thr Leu His Gly Pro Phe
        195                 200                 205

Phe Ser Ser Phe Ala Cys Val Val Cys Tyr Lys Lys Phe Val Thr Gln
    210                 215                 220

Gln Gln Tyr Arg Asp His Leu Phe Asp Lys Glu Ala Thr Asp Asp Gly
225                 230                 235                 240

His Asn Asn Asn Leu Leu Pro Gln Ile Ile Gln Cys Phe Ala Cys Pro
                245                 250                 255

Asn Cys Phe Leu Leu Phe Ser Arg Lys Glu Glu Cys Ser Lys His Met
            260                 265                 270

Ser Gly Lys Asn His Phe His Gln Ser Phe Lys Leu Gly Asp Asn Lys
        275                 280                 285

Gly Ile Ala His Pro Ile Ser Phe Pro Ser Phe Ala Lys Lys Leu Leu
    290                 295                 300

Ile Ser Leu Cys Lys Asp Val Pro Phe Gln Val Lys Cys Val Ala Cys
305                 310                 315                 320
```

-continued

```
His Lys Thr Leu Arg Ser His Met Glu Leu Thr Ala His Phe Arg Val
                325                 330                 335

His Cys Arg Asn Ala Gly Pro Val Ala Val Ala Glu Lys Ser Ile Thr
            340                 345                 350

Gln Val Ala Glu Lys Phe Ile Leu Arg Gly Tyr Cys Pro Asp Cys Asn
        355                 360                 365

Gln Val Phe Val Asp Glu Thr Ser Thr Gln Asn His Lys Gln Asn Ser
    370                 375                 380

Gly His Lys Val Arg Val Ile Asn Ser Val Glu Glu Ser Val Leu Leu
385                 390                 395                 400

Tyr Cys His Ser Ser Glu Gly Asn Lys Asp Pro Ser Ser Asp Leu His
            405                 410                 415

Leu Leu Leu Asp Gln Ser Lys Phe Ser Ser Leu Lys Arg Thr Met Ser
        420                 425                 430

Ile Lys Glu Ser Ser Ser Leu Glu Cys Ile Ala Ile Pro Lys Lys Lys
    435                 440                 445

Met Asn Leu Lys Asp Lys Ser His Glu Gly Val Ala Cys Val Gln Lys
    450                 455                 460

Glu Lys Ser Val Val Lys Thr Trp Phe Cys Glu Cys Asn Gln Arg Phe
465                 470                 475                 480

Pro Ser Glu Asp Ala Val Glu Lys His Val Phe Ser Ala Asn Thr Met
            485                 490                 495

Gly Tyr Lys Cys Val Val Cys Gly Lys Val Cys Asp Asp Ser Gly Val
        500                 505                 510

Ile Arg Leu His Met Ser Arg Ile His Gly Gly Ala His Leu Asn Asn
    515                 520                 525

Phe Leu Phe Trp Cys Arg Thr Cys Lys Lys Glu Leu Thr Arg Lys Asp
    530                 535                 540

Thr Ile Met Ala His Val Thr Glu Phe His Asn Gly His Arg Tyr Phe
545                 550                 555                 560

Tyr Glu Met Asp Glu Val Gly Glu Thr Leu Pro Ser Ser Ser Thr
            565                 570                 575

Thr Leu Asp Asn Leu Thr Ala Asn Lys Pro Ser Ser Ala Ile Thr Val
        580                 585                 590

Ile Asp His Ser Pro Ala Asn Ser Ser Pro Arg Gly Lys Trp Gln Cys
    595                 600                 605

Arg Ile Cys Glu Asp Met Phe Asp Ser Gln Glu Tyr Val Lys Gln His
    610                 615                 620

Cys Met Ser Leu Ala Ser His Lys Phe His Arg Tyr Ser Cys Ala His
625                 630                 635                 640

Cys Arg Lys Pro Phe His Lys Ile Glu Thr Leu Tyr Arg His Cys Gln
            645                 650                 655

Asp Glu His Asp Asn Glu Ile Lys Ile Lys Tyr Phe Cys Gly Leu Cys
        660                 665                 670

Asp Leu Ile Phe Asn Val Glu Glu Ala Phe Leu Ser His Tyr Glu Glu
    675                 680                 685

His His Ser Ile Asp Tyr Val Phe Val Ser Glu Lys Thr Glu Thr Ser
    690                 695                 700

Ile Lys Thr Glu Asp Asp Phe Pro Val Ile Glu Thr Ser Asn Gln Leu
705                 710                 715                 720

Thr Cys Gly Cys Arg Glu Ser Tyr Ile Cys Lys Val Asn Arg Lys Glu
            725                 730                 735

Asp Tyr Ser Arg Cys Leu Gln Ile Met Leu Asp Lys Gly Lys Leu Trp
```

-continued

```
                740                 745                 750
Phe Arg Cys Ser Leu Cys Ser Ala Thr Ala Gln Asn Leu Thr Asp Met
            755                 760                 765

Asn Thr His Ile His Gln Val His Lys Glu Lys Ser Asp Glu Glu Glu
        770                 775                 780

Gln Gln Tyr Val Ile Lys Cys Gly Thr Cys Thr Lys Ala Phe His Asp
785                 790                 795                 800

Pro Glu Ser Ala Gln Gln His Phe His Arg Lys His Cys Phe Leu Gln
            805                 810                 815

Lys Pro Ser Val Ala His Phe Gly Ser Glu Lys Ser Asn Leu Tyr Lys
        820                 825                 830

Phe Thr Ala Ser Ala Ser His Thr Glu Arg Lys Leu Lys Gln Ala Ile
        835                 840                 845

Asn Tyr Ser Lys Ser Leu Asp Met Glu Lys Gly Val Glu Asn Asp Leu
        850                 855                 860

Ser Tyr Gln Asn Ile Glu Glu Ile Val Leu Pro Asp Leu Asp
865                 870                 875                 880

Tyr Leu Arg Thr Met Thr His Ile Val Phe Val Asp Phe Asp Asn Trp
            885                 890                 895

Ser Asn Phe Phe Gly His Leu Pro Gly His Leu Asn Gln Gly Thr Phe
        900                 905                 910

Ile Trp Gly Phe Gln Gly Gly Asn Thr Asn Trp Lys Pro Pro Leu Asn
        915                 920                 925

Cys Lys Ile Tyr Asn Tyr Leu Asn Arg Ile Gly Cys Phe Phe Leu His
        930                 935                 940

Pro Arg Cys Ser Lys Arg Lys Asp Ala Ala Asp Phe Ala Ile Cys Met
945                 950                 955                 960

His Ala Gly Arg Leu Asp Glu Gln Leu Pro Lys Gln Ile Pro Phe Thr
            965                 970                 975

Ile Leu Ser Gly Asp Gln Gly Phe Leu Glu Leu Glu Asn Gln Phe Lys
        980                 985                 990

Lys Thr Gln Arg Pro Ala His Ile Leu Asn Pro His His Leu Glu Gly
        995                 1000                1005

Asp Met Met Cys Ala Leu Leu Asn Ser Ile Ser Asp Thr Thr Lys Glu
    1010                1015                1020

Cys Asp Ser Asp Asp Asn Met Gly Ala Lys Asn Thr Ser Ile Gly Glu
1025                1030                1035                1040

Glu Phe Ile Ser Thr Glu Asp Val Glu Leu Glu Ala Ile Arg Arg
            1045                1050                1055

Ser Leu Glu Glu Met
        1060

<210> SEQ ID NO 12
<211> LENGTH: 1061
<212> TYPE: PRT
<213> ORGANISM: Homo sapiens

<400> SEQUENCE: 12

Met Gly Asp Pro Gly Ser Glu Ile Ile Glu Ser Val Pro Ala Gly
1               5                   10                  15

Pro Glu Ala Ser Glu Ser Thr Thr Asp Glu Asn Glu Asp Asp Ile Gln
            20                  25                  30

Phe Val Ser Glu Gly Pro Leu Arg Pro Val Leu Glu Tyr Ile Asp Leu
        35                  40                  45
```

```
Val Ser Ser Asp Asp Glu Glu Pro Ser Thr Ser Tyr Thr Asp Glu Asn
     50                  55                  60

Ile Lys Arg Lys Asp His Ile Asp Tyr Gln Lys Asp Lys Val Ala Leu
 65                  70                  75                  80

Thr Leu Ala Arg Leu Ala Arg His Val Glu Val Glu Lys Gln Gln Lys
                 85                  90                  95

Glu Glu Lys Asn Arg Ala Phe Arg Glu Lys Ile Asp Phe Gln His Ala
             100                 105                 110

His Gly Leu Gln Glu Leu Glu Phe Ile Arg Gly His Ser Asp Thr Glu
             115                 120                 125

Ala Ala Arg Leu Cys Val Asp Gln Trp Leu Lys Met Pro Gly Leu Lys
         130                 135                 140

Thr Gly Thr Ile Asn Cys Gly Thr Lys Ser Ser Phe Arg Arg Gly Gly
145                 150                 155                 160

His Thr Trp Val Ser Gly Lys Pro Thr Leu Cys Pro Ile Met His Cys
                     165                 170                 175

Asn Lys Glu Phe Asp Asn Gly His Leu Leu Leu Gly His Leu Lys Arg
                 180                 185                 190

Phe Asp His Ser Pro Cys Asp Pro Thr Ile Thr Leu His Gly Pro Phe
             195                 200                 205

Phe Ser Ser Phe Ala Cys Val Val Cys Tyr Lys Lys Phe Val Thr Gln
         210                 215                 220

Gln Gln Tyr Arg Asp His Leu Phe Asp Lys Glu Ala Thr Asp Asp Gly
225                 230                 235                 240

His Asn Asn Asn Leu Leu Pro Gln Ile Ile Gln Cys Phe Ala Cys Pro
                     245                 250                 255

Asn Cys Phe Leu Leu Phe Ser Arg Lys Glu Glu Cys Ser Lys His Met
                 260                 265                 270

Ser Gly Lys Asn His Phe His Gln Ser Phe Lys Leu Gly Asp Asn Lys
             275                 280                 285

Gly Ile Ala His Pro Ile Ser Phe Pro Ser Phe Ala Lys Lys Leu Leu
         290                 295                 300

Ile Ser Leu Cys Lys Asp Val Pro Phe Gln Val Lys Cys Val Ala Cys
305                 310                 315                 320

His Lys Thr Leu Arg Ser His Met Glu Leu Thr Ala His Phe Arg Val
                     325                 330                 335

His Cys Arg Asn Ala Gly Pro Val Ala Val Ala Glu Lys Ser Ile Thr
                 340                 345                 350

Gln Val Ala Glu Lys Phe Ile Leu Arg Gly Tyr Cys Pro Asp Cys Asn
             355                 360                 365

Gln Val Phe Val Asp Glu Thr Ser Thr Gln Asn His Lys Gln Asn Ser
         370                 375                 380

Gly His Lys Val Arg Val Ile Asn Ser Val Glu Glu Ser Val Leu Leu
385                 390                 395                 400

Tyr Cys His Ser Ser Glu Gly Asn Lys Asp Pro Ser Ser Asp Leu His
                     405                 410                 415

Leu Leu Leu Asp Gln Ser Lys Phe Ser Ser Leu Lys Arg Thr Met Ser
                 420                 425                 430

Ile Lys Glu Ser Ser Ser Leu Glu Cys Ile Ala Ile Pro Lys Lys Lys
             435                 440                 445

Met Asn Leu Lys Asp Lys Ser His Glu Gly Val Ala Cys Val Gln Lys
         450                 455                 460

Glu Lys Ser Val Val Lys Thr Trp Phe Cys Glu Cys Asn Gln Arg Phe
```

```
                465                 470                 475                 480
Pro Ser Glu Asp Ala Val Glu Lys His Val Phe Ser Ala Asn Thr Met
                    485                 490                 495
Gly Tyr Lys Cys Val Val Cys Gly Lys Val Cys Asp Asp Ser Gly Val
                500                 505                 510
Ile Arg Leu His Met Ser Arg Ile His Gly Gly Ala His Leu Asn Asn
            515                 520                 525
Phe Leu Phe Trp Cys Arg Thr Cys Lys Lys Glu Leu Thr Arg Lys Asp
        530                 535                 540
Thr Ile Met Ala His Val Thr Glu Phe His Asn Gly His Arg Tyr Phe
545                 550                 555                 560
Tyr Glu Met Asp Glu Val Glu Gly Glu Thr Leu Pro Ser Ser Ser Thr
                565                 570                 575
Thr Leu Asp Asn Leu Thr Ala Asn Lys Pro Ser Ser Ala Ile Thr Val
            580                 585                 590
Ile Asp His Ser Pro Ala Asn Ser Ser Pro Arg Gly Lys Trp Gln Cys
        595                 600                 605
Arg Ile Cys Glu Asp Met Phe Asp Ser Gln Glu Tyr Val Lys Gln His
    610                 615                 620
Cys Met Ser Leu Ala Ser His Lys Phe His Arg Tyr Ser Cys Ala His
625                 630                 635                 640
Cys Arg Lys Pro Phe His Lys Ile Glu Thr Leu Tyr Arg His Cys Gln
                645                 650                 655
Asp Glu His Asp Asn Glu Ile Lys Ile Lys Tyr Phe Cys Gly Leu Cys
            660                 665                 670
Asp Leu Ile Phe Asn Val Glu Glu Ala Phe Leu Ser His Tyr Glu Glu
        675                 680                 685
His His Ser Ile Asp Tyr Val Phe Val Ser Glu Lys Thr Glu Thr Ser
    690                 695                 700
Ile Lys Thr Glu Asp Asp Phe Pro Val Ile Glu Thr Ser Asn Gln Leu
705                 710                 715                 720
Thr Cys Gly Cys Arg Glu Ser Tyr Ile Cys Lys Val Asn Arg Lys Glu
                725                 730                 735
Asp Tyr Ser Arg Cys Leu Gln Ile Met Leu Asp Lys Gly Lys Leu Trp
            740                 745                 750
Phe Arg Cys Ser Leu Cys Ser Ala Thr Ala Gln Asn Leu Thr Asp Met
        755                 760                 765
Asn Thr His Ile His Gln Val His Lys Glu Lys Ser Asp Glu Glu Glu
    770                 775                 780
Gln Gln Tyr Val Ile Lys Cys Gly Thr Cys Thr Lys Ala Phe His Asp
785                 790                 795                 800
Pro Glu Ser Ala Gln Gln His Phe Arg Lys His Cys Phe Leu Gln
                805                 810                 815
Lys Pro Ser Val Ala His Phe Gly Ser Glu Lys Ser Asn Leu Tyr Lys
            820                 825                 830
Phe Thr Ala Ser Ala Ser His Thr Glu Arg Lys Leu Lys Gln Ala Ile
        835                 840                 845
Asn Tyr Ser Lys Ser Leu Asp Met Glu Lys Gly Val Glu Asn Asp Leu
    850                 855                 860
Ser Tyr Gln Asn Ile Glu Glu Ile Val Glu Leu Pro Asp Leu Asp
865                 870                 875                 880
Tyr Leu Arg Thr Met Thr His Ile Val Phe Val Asp Phe Asp Asn Trp
                885                 890                 895
```

```
Ser Asn Phe Phe Gly His Leu Pro Gly His Leu Asn Gln Gly Thr Phe
            900                 905                 910

Ile Trp Gly Phe Gln Gly Gly Asn Thr Asn Trp Lys Pro Pro Leu Asn
        915                 920                 925

Cys Lys Ile Tyr Asn Tyr Leu Asn Arg Ile Gly Cys Phe Phe Leu His
        930                 935                 940

Pro Arg Cys Ser Lys Arg Lys Asp Ala Ala Asp Phe Ala Ile Cys Met
945                 950                 955                 960

His Ala Gly Arg Leu Asp Glu Gln Leu Pro Lys Gln Ile Pro Phe Thr
                965                 970                 975

Ile Leu Ser Gly Asp Gln Gly Phe Leu Glu Leu Glu Asn Gln Phe Lys
            980                 985                 990

Lys Thr Gln Arg Pro Ala His Ile Leu Asn Pro His His Leu Glu Gly
        995                 1000                1005

Asp Met Met Cys Ala Leu Leu Asn Ser Ile Ser Asp Thr Thr Lys Glu
    1010                1015                1020

Cys Asp Ser Asp Asp Asn Met Gly Ala Lys Asn Thr Ser Ile Gly Glu
1025                1030                1035                1040

Glu Phe Ile Ser Thr Glu Asp Val Glu Leu Glu Ala Ile Arg Arg
                1045                1050                1055

Ser Leu Glu Glu Met
            1060

<210> SEQ ID NO 13
<211> LENGTH: 19
<212> TYPE: DNA
<213> ORGANISM: Homo sapiens

<400> SEQUENCE: 13
atgggagacc cgggtcgga                                                  19

<210> SEQ ID NO 14
<211> LENGTH: 20
<212> TYPE: DNA
<213> ORGANISM: Homo sapiens

<400> SEQUENCE: 14
ttacatttcc tcaagacttc                                                 20

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 15
ctaggtaccg gacagcagga gcagtggtgc                                      30

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
ggcagtgagc tccatgtggg                                                 20
```